(12) United States Patent
Butler et al.

(10) Patent No.: US 8,092,494 B2
(45) Date of Patent: Jan. 10, 2012

(54) PEDICLE SCREW CONSTRUCTS FOR SPINE FIXATION SYSTEMS

(75) Inventors: Michael S. Butler, Fishers, IN (US); Jim A. Youssef, Durango, CO (US); Alan S. Hilibrand, Merion Station, PA (US)

(73) Assignee: Life Spine, Inc., Hoffman Estates, IL (US)

( * ) Notice: Subject to any disclaimer, the term of this patent is extended or adjusted under 35 U.S.C. 154(b) by 1200 days.

(21) Appl. No.: 11/829,814

(22) Filed: Jul. 27, 2007

(65) Prior Publication Data

US 2008/0021473 A1 Jan. 24, 2008

Related U.S. Application Data

(63) Continuation of application No. 11/034,300, filed on Jan. 12, 2005, now Pat. No. 7,678,137.

(60) Provisional application No. 60/536,319, filed on Jan. 13, 2004.

(51) Int. Cl.
*A61B 17/70* (2006.01)

(52) U.S. Cl. ...................................... 606/246

(58) Field of Classification Search .................. 606/246, 606/251–279
See application file for complete search history.

(56) References Cited

U.S. PATENT DOCUMENTS

| | | | |
|---|---|---|---|
| 2,414,882 A | 1/1947 | Longfellow | |
| 4,399,814 A | 8/1983 | Pratt, Jr. et al. | |
| 4,648,388 A | 3/1987 | Steffee | |
| 4,653,489 A | 3/1987 | Tronzo | |
| 4,790,297 A | 12/1988 | Luque | |
| 4,805,602 A | 2/1989 | Puno et al. | |
| 4,863,472 A | 9/1989 | Tormala et al. | |
| 5,002,542 A | 3/1991 | Frigg | |
| 5,030,220 A | 7/1991 | Howland | |
| 5,047,029 A | 9/1991 | Aebi et al. | |

(Continued)

FOREIGN PATENT DOCUMENTS

WO WO 02/36026 5/2002

(Continued)

OTHER PUBLICATIONS

"The Trio® Spinal System," printed Feb. 9, 2005, 2 pages.

(Continued)

*Primary Examiner* — Thomas C. Barrett
*Assistant Examiner* — Michael Araj
(74) *Attorney, Agent, or Firm* — Foley & Lardner LLP

(57) ABSTRACT

A pedicle screw coupling construct for a pedicle screw construct provides fixation of angular orientation thereof relative to a pedicle screw independent of fixation of a received spinal rod to the coupling construct. The pedicle screw construct forms one component or element in a spinal fixation system. The independent fixation coupling construct also provides for fixation of the angular orientation of the coupling construct while the coupling construct has received the spinal rod. In another form, a coupling head or construct is configured to allow a pedicle screw shaft to pass therethrough but retain the pedicle screw head for rotation of the coupling head about the pedicle screw head. The coupling head or construct is also configured to allow at least a 45° arc of pivot or articulation about a pedicle screw shaft relative to a longitudinal axis of a spinal rod received in the body. This allows the head with a received spinal rod to fold, bend or pivot relative to the pedicle screw shaft, particularly to a greater degree than the prior art.

19 Claims, 13 Drawing Sheets

U.S. PATENT DOCUMENTS

| | | |
|---|---|---|
| 5,092,893 A | 3/1992 | Smith |
| 5,098,435 A | 3/1992 | Stednitz et al. |
| 5,122,131 A | 6/1992 | Tsou |
| 5,129,899 A | 7/1992 | Small et al. |
| 5,176,680 A * | 1/1993 | Vignaud et al. ............... 606/302 |
| 5,222,954 A | 6/1993 | Baker et al. |
| 5,242,445 A | 9/1993 | Ashman |
| 5,246,442 A | 9/1993 | Ashman et al. |
| 5,261,909 A | 11/1993 | Sutterlin et al. |
| 5,281,222 A | 1/1994 | Allard et al. |
| 5,282,801 A | 2/1994 | Sherman |
| 5,282,862 A | 2/1994 | Baker et al. |
| 5,344,422 A | 9/1994 | Frigg |
| 5,350,380 A | 9/1994 | Goble et al. |
| 5,352,226 A | 10/1994 | Lin |
| 5,360,431 A | 11/1994 | Puno et al. |
| 5,403,316 A | 4/1995 | Ashman |
| 5,423,818 A | 6/1995 | Van Hoeck et al. |
| 5,423,819 A | 6/1995 | Small et al. |
| 5,437,669 A | 8/1995 | Yuan et al. |
| 5,437,670 A | 8/1995 | Sherman et al. |
| 5,449,257 A | 9/1995 | Giannuzzi |
| 5,466,237 A | 11/1995 | Byrd, III et al. |
| 5,474,551 A | 12/1995 | Finn et al. |
| 5,474,555 A | 12/1995 | Puno et al. |
| 5,496,321 A | 3/1996 | Puno et al. |
| 5,520,690 A | 5/1996 | Errico et al. |
| 5,527,314 A | 6/1996 | Brumfield et al. |
| 5,534,002 A | 7/1996 | Brumfield et al. |
| 5,545,163 A | 8/1996 | Miller |
| 5,562,661 A | 10/1996 | Yoshimi et al. |
| 5,562,662 A | 10/1996 | Brumfield et al. |
| 5,569,252 A | 10/1996 | Justin et al. |
| 5,575,792 A | 11/1996 | Errico et al. |
| 5,578,033 A | 11/1996 | Errico et al. |
| 5,582,612 A | 12/1996 | Lin |
| 5,584,833 A | 12/1996 | Fournet-Fayard et al. |
| 5,584,834 A | 12/1996 | Errico et al. |
| 5,609,593 A | 3/1997 | Errico et al. |
| 5,609,594 A | 3/1997 | Errico et al. |
| 5,611,800 A | 3/1997 | Davis et al. |
| 5,616,142 A | 4/1997 | Yuan et al. |
| 5,643,262 A | 7/1997 | Metz-Stavenhagen et al. |
| 5,647,873 A | 7/1997 | Errico et al. |
| 5,649,931 A | 7/1997 | Bryant et al. |
| 5,667,513 A | 9/1997 | Torrie et al. |
| 5,669,911 A | 9/1997 | Errico et al. |
| 5,672,176 A * | 9/1997 | Biedermann et al. ......... 606/271 |
| 5,688,275 A | 11/1997 | Koros et al. |
| 5,690,630 A | 11/1997 | Errico et al. |
| 5,713,904 A | 2/1998 | Errico et al. |
| 5,733,285 A | 3/1998 | Errico et al. |
| 5,752,957 A | 5/1998 | Ralph et al. |
| 5,776,135 A | 7/1998 | Errico et al. |
| 5,782,833 A * | 7/1998 | Haider ........................ 606/266 |
| 5,810,818 A | 9/1998 | Errico et al. |
| 5,810,819 A | 9/1998 | Errico et al. |
| 5,817,094 A | 10/1998 | Errico et al. |
| 5,873,878 A * | 2/1999 | Harms et al. .................. 606/308 |
| 5,884,702 A | 3/1999 | Simson |
| 5,899,904 A | 5/1999 | Errico et al. |
| 5,899,905 A | 5/1999 | Errico et al. |
| 5,938,663 A | 8/1999 | Petreto |
| 5,941,885 A | 8/1999 | Jackson |
| 5,947,967 A | 9/1999 | Barker |
| 5,951,558 A | 9/1999 | Fiz |
| 5,961,518 A | 10/1999 | Errico et al. |
| 5,976,135 A | 11/1999 | Sherman et al. |
| 5,997,539 A | 12/1999 | Errico et al. |
| 6,001,098 A | 12/1999 | Metz-Stavenhagen et al. |
| 6,016,727 A | 1/2000 | Morgan |
| 6,017,344 A | 1/2000 | Errico et al. |
| 6,030,388 A | 2/2000 | Yoshimi et al. |
| 6,033,406 A | 3/2000 | Mathews |
| 6,045,555 A | 4/2000 | Smith et al. |
| 6,048,343 A | 4/2000 | Mathis et al. |
| 6,059,785 A | 5/2000 | Schavan et al. |
| 6,063,089 A | 5/2000 | Errico et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,096,060 A | 8/2000 | Fitts et al. |
| 6,111,164 A | 8/2000 | Rainey et al. |
| 6,123,706 A | 9/2000 | Lange |
| 6,132,430 A | 10/2000 | Wagner |
| 6,139,549 A | 10/2000 | Keller |
| 6,159,210 A | 12/2000 | Voor |
| 6,179,838 B1 | 1/2001 | Fiz |
| 6,183,473 B1 | 2/2001 | Ashman |
| 6,193,721 B1 | 2/2001 | Michelson |
| 6,210,376 B1 | 4/2001 | Grayson |
| 6,210,413 B1 | 4/2001 | Justis et al. |
| 6,224,602 B1 | 5/2001 | Hayes |
| 6,228,085 B1 | 5/2001 | Theken et al. |
| 6,231,575 B1 | 5/2001 | Krag |
| 6,234,705 B1 | 5/2001 | Troxell |
| 6,248,104 B1 | 6/2001 | Chopin et al. |
| 6,248,105 B1 | 6/2001 | Schlapfer et al. |
| 6,248,107 B1 | 6/2001 | Foley et al. |
| 6,254,602 B1 | 7/2001 | Justis |
| 6,258,089 B1 | 7/2001 | Campbell et al. |
| 6,261,287 B1 | 7/2001 | Metz-Stavenhagen |
| 6,273,889 B1 | 8/2001 | Richelsoph |
| 6,280,442 B1 | 8/2001 | Barker et al. |
| 6,283,967 B1 | 9/2001 | Troxell et al. |
| 6,302,888 B1 | 10/2001 | Mellinger et al. |
| 6,306,136 B1 | 10/2001 | Baccelli |
| 6,306,137 B2 | 10/2001 | Troxell |
| 6,315,779 B1 | 11/2001 | Morrison et al. |
| 6,317,957 B1 | 11/2001 | Gregor et al. |
| 6,355,039 B1 | 3/2002 | Troussel et al. |
| RE37,665 E | 4/2002 | Ralph et al. |
| 6,364,881 B1 | 4/2002 | Apgar et al. |
| 6,371,957 B1 | 4/2002 | Amrein et al. |
| 6,379,357 B1 | 4/2002 | Bernstein et al. |
| 6,398,783 B1 | 6/2002 | Michelson |
| 6,402,749 B1 | 6/2002 | Ashman |
| 6,402,756 B1 | 6/2002 | Ralph et al. |
| 6,413,259 B1 | 7/2002 | Lyons et al. |
| 6,416,515 B1 | 7/2002 | Wagner |
| 6,428,542 B1 | 8/2002 | Michelson |
| 6,454,769 B2 | 9/2002 | Wagner et al. |
| 6,471,703 B1 | 10/2002 | Ashman |
| 6,503,250 B2 | 1/2003 | Paul |
| 6,533,786 B1 | 3/2003 | Needham et al. |
| 6,537,276 B2 | 3/2003 | Metz-Stavenhagen |
| 6,554,834 B1 | 4/2003 | Crozet et al. |
| 6,562,040 B1 | 5/2003 | Wagner |
| 6,565,565 B1 | 5/2003 | Yuan et al. |
| 6,582,436 B2 | 6/2003 | Schlapfer et al. |
| 6,599,290 B2 | 7/2003 | Bailey et al. |
| 6,602,257 B1 | 8/2003 | Thramann |
| 6,613,050 B1 | 9/2003 | Wagner et al. |
| 6,616,665 B2 | 9/2003 | Grafton et al. |
| 6,620,163 B1 | 9/2003 | Michelson |
| 6,626,904 B1 | 9/2003 | Jammet et al. |
| 6,626,906 B1 | 9/2003 | Young |
| 6,626,908 B2 | 9/2003 | Cooper et al. |
| 6,641,583 B2 | 11/2003 | Shluzas et al. |
| 6,641,586 B2 | 11/2003 | Varieur |
| 6,648,887 B2 | 11/2003 | Ashman |
| 6,648,894 B2 | 11/2003 | Abdelgany et al. |
| 6,660,004 B2 | 12/2003 | Barker et al. |
| 6,663,642 B2 | 12/2003 | Beyar et al. |
| 6,668,688 B2 | 12/2003 | Zhao et al. |
| 6,669,700 B1 | 12/2003 | Farris et al. |
| 6,673,073 B1 | 1/2004 | Schafer |
| 6,676,661 B1 | 1/2004 | MartinBenlloch et al. |
| 6,685,705 B1 | 2/2004 | Taylor |
| 6,695,846 B2 | 2/2004 | Richelsoph et al. |
| 6,706,045 B2 | 3/2004 | Lin et al. |
| 6,716,214 B1 | 4/2004 | Jackson |
| 6,723,100 B2 | 4/2004 | Biedermann et al. |
| 6,733,502 B2 | 5/2004 | Altarac et al. |
| 6,736,817 B2 | 5/2004 | Troxell et al. |
| 6,755,830 B2 | 6/2004 | Minfelde et al. |
| 6,755,835 B2 | 6/2004 | Schultheiss et al. |

| | | |
|---|---|---|
| 6,786,907 B2 | 9/2004 | Lange |
| 6,827,722 B1 | 12/2004 | Schoenefeld |
| 6,832,999 B2 | 12/2004 | Ueyama et al. |
| 6,835,196 B2 | 12/2004 | Biedermann et al. |
| 6,858,030 B2 | 2/2005 | Martin et al. |
| 6,893,444 B2 | 5/2005 | Orbay |
| 6,899,714 B2 | 5/2005 | Vaughan |
| 6,949,100 B1 | 9/2005 | Venturini |
| 6,951,561 B2 | 10/2005 | Warren et al. |
| 6,974,460 B2 | 12/2005 | Carbone et al. |
| 7,678,137 B2 | 3/2010 | Butler et al. |
| 7,744,635 B2 | 6/2010 | Sweeney et al. |
| 2001/0041894 A1 | 11/2001 | Campbell et al. |
| 2002/0045896 A1 | 4/2002 | Michelson |
| 2002/0045899 A1 | 4/2002 | Errico et al. |
| 2002/0111630 A1 | 8/2002 | Ralph et al. |
| 2002/0120273 A1 | 8/2002 | Needham et al. |
| 2002/0128655 A1 | 9/2002 | Michelson |
| 2002/0143332 A1 | 10/2002 | Lin et al. |
| 2002/0143341 A1 | 10/2002 | Biedermann et al. |
| 2002/0147450 A1 | 10/2002 | LeHuec et al. |
| 2002/0151899 A1 | 10/2002 | Bailey et al. |
| 2002/0169450 A1 | 11/2002 | Lange |
| 2002/0183748 A1 | 12/2002 | Martin et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2002/0193794 A1 | 12/2002 | Taylor |
| 2003/0000350 A1 | 1/2003 | Zhao et al. |
| 2003/0004511 A1 | 1/2003 | Ferree |
| 2003/0004512 A1 | 1/2003 | Farris et al. |
| 2003/0023240 A1 | 1/2003 | Amrein et al. |
| 2003/0023242 A1 | 1/2003 | Harrington, Jr. |
| 2003/0040749 A1 | 2/2003 | Grabowski et al. |
| 2003/0045878 A1 | 3/2003 | Petit et al. |
| 2003/0055426 A1 | 3/2003 | Carbone et al. |
| 2003/0060828 A1 | 3/2003 | Michelson |
| 2003/0073997 A1 | 4/2003 | Doubler et al. |
| 2003/0083658 A1 | 5/2003 | Hawkes et al. |
| 2003/0105460 A1 | 6/2003 | Crandall et al. |
| 2003/0105462 A1 | 6/2003 | Haider |
| 2003/0125741 A1 | 7/2003 | Biedermann et al. |
| 2003/0149431 A1 | 8/2003 | Varieur |
| 2003/0149432 A1 | 8/2003 | Frigg et al. |
| 2003/0171751 A1 | 9/2003 | Ritland |
| 2003/0176862 A1 | 9/2003 | Taylor et al. |
| 2003/0191473 A1 | 10/2003 | Taylor |
| 2003/0208202 A1 | 11/2003 | Falahee |
| 2004/0010253 A1 | 1/2004 | Morrison |
| 2004/0034356 A1 | 2/2004 | LeHuec et al. |
| 2004/0039383 A1 | 2/2004 | Jackson |
| 2004/0068319 A1 | 4/2004 | Cordaro |
| 2004/0087951 A1 | 5/2004 | Khalili |
| 2004/0092930 A1 | 5/2004 | Petit et al. |
| 2004/0102773 A1 | 5/2004 | Morrison et al. |
| 2004/0102780 A1 | 5/2004 | West, Jr. |
| 2004/0106924 A1 | 6/2004 | Ralph et al. |
| 2004/0122425 A1 | 6/2004 | Suzuki et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127899 A1 | 7/2004 | Konieczynski et al. |
| 2004/0138662 A1 | 7/2004 | Landry et al. |
| 2004/0147928 A1 | 7/2004 | Landry et al. |
| 2004/0153068 A1 | 8/2004 | Janowski et al. |
| 2004/0158247 A1 | 8/2004 | Sitiso et al. |
| 2004/0181226 A1 | 9/2004 | Michelson |
| 2004/0181229 A1 | 9/2004 | Michelson |
| 2004/0186474 A1 | 9/2004 | Matthis et al. |
| 2004/0186476 A1 | 9/2004 | Michelson |
| 2004/0204712 A1 | 10/2004 | Kolb et al. |
| 2004/0215190 A1 | 10/2004 | Nguyen et al. |
| 2004/0220571 A1 | 11/2004 | Assaker et al. |
| 2004/0220572 A1 | 11/2004 | Michelson |
| 2004/0236335 A1 | 11/2004 | Michelson |
| 2004/0243139 A1 | 12/2004 | Lewis et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0043732 A1 | 2/2005 | Dalton |
| 2005/0059971 A1 | 3/2005 | Michelson |
| 2005/0075699 A1 | 4/2005 | Olson et al. |
| 2005/0113830 A1 | 5/2005 | Rezach et al. |
| 2005/0113833 A1 | 5/2005 | Davison |
| 2005/0149026 A1 | 7/2005 | Butler et al. |
| 2005/0277923 A1 | 12/2005 | Sweeney |
| 2005/0277931 A1 | 12/2005 | Sweeney et al. |
| 2006/0079903 A1 | 4/2006 | Wong |
| 2006/0089647 A1 | 4/2006 | Culbert et al. |
| 2006/0149234 A1 | 7/2006 | de Coninck |
| 2006/0195096 A1 | 8/2006 | Lee et al. |
| 2006/0224241 A1 | 10/2006 | Butler et al. |
| 2007/0118122 A1 | 5/2007 | Butler et al. |
| 2007/0161996 A1 | 7/2007 | Biedermann et al. |
| 2007/0173833 A1 | 7/2007 | Butler et al. |
| 2008/0024173 A1 | 1/2008 | Nagai et al. |

FOREIGN PATENT DOCUMENTS

| | | |
|---|---|---|
| WO | WO 03/028538 | 4/2003 |
| WO | WO 2005/122965 | 12/2005 |

OTHER PUBLICATIONS

Chen, Pei-Yu et al., "Closed Reduction With Intramedullary Fixation for Midclavicular Fractures," Orthopedics Journal, May 2004, pp. 459-462, vol. 27, No. 5.

Lamendola, Mark, How to Use Belleville Washers Correctly, Dec. 1, 1997, EC&M, 2 pages.

* cited by examiner

PEDICLE SCREW CONSTRUCTS FOR SPINE FIXATION SYSTEMS

This U.S. non-provisional patent application is a continuation of U.S. patent application Ser. No. 11/034,300 titled "PEDICLE SCREW CONSTRUCTS FOR SPINE FIXATION SYSTEMS" filed Jan. 12, 2005, the full disclosure of which is hereby incorporated herein by reference; which claims the benefit of and/or priority to U.S. provisional patent application Ser. No. 60/536,319 filed Jan. 13, 2004 entitled "Pedicle Screw Construct for a Spine Fixation System", the entire contents of which is specifically incorporated herein by reference.

BACKGROUND OF THE INVENTION

The present invention relates generally to spinal fixation devices for the internal fixation of the spine particularly within the fields of orthopedics and/or neurosurgery such as spinal implants and rods for holding vertebral bones fixed relative to one another and, more particularly, to a polyaxial pedicle screw and/or coupling apparatus for use in spinal surgical procedures for receiving a rod for stabilizing the relative motion of vertebrae.

The spinal column of bones is a highly complex structure that not only allows a high degree of flexible movement in various directions, but also envelopes and protects numerous veins, arteries and nerves of the body. The adult human spine consists of over twenty discrete bones that are coupled sequentially to one another through posterior facet joints and discs of cartilage (known as intervertebral discs or simply, discs) positioned between adjacent vertebrae. The facet joints and discs allow the spine to bend and twist. Different muscles coordinate movement in many directions.

Areas of the spine have been anatomically categorized. Thus, bones of the spine are anatomically classified as being from one of four areas or classifications, namely, the cervical, thoracic, lumbar, or sacral areas. The various areas of the spine also have a natural or characteristic curvature or curve. The four curves of the spine are known as the cervical lordosis, the thoracic kyphosis, the lumber lordosis and the sacral kyphosis.

Genetic or irregularities such as developmental irregularities, trauma, tumors, disease and the like, however, can result in spinal pathologies that either limit the range of normal spinal motion or that threatens the integrity of elements of the nervous, circulatory and/or other systems of the spine. In these cases and others such as spinal curvature problems, a spinal fixation system may be used in order to immobilize various vertebrae. Various systems have been devised to provide the necessary vertebrae immobilization. These spinal fixation systems are implanted on or in the spine (spinal column). Such spinal fixation systems or assemblies may be classified as anterior, posterior or lateral implants. Lateral and anterior fixation assemblies are attached to the lateral and anterior portions of the spine. Posterior implants generally include a pair of rods that are along the axis to which the vertebrae are to be disposed and then attached to the vertebrae by either hooks that couple to the lamina or transverse process of the vertebrae, or by screws that are inserted into the pedicles thereof.

Rod assemblies as spinal fixation systems generally comprise a plurality of bone or pedicle screws that are implanted into the posterior lateral surfaces of the laminae, through the pedicles and into their respective vertebral bodies. Each screw includes a coupling device for receiving and retaining a section of a spinal rod. The rod extends along the axis of the spine being attached to the plurality of pedicle screws through their respective coupling device. The rigidity of the spinal rod may be utilized to align the spine in conformance with a desired shape.

Considerable difficulty, however, was encountered with inserting fixed screws along a misaligned curvature and then simultaneously exactly positioning the coupling devices such that the spinal rod receiving portions of the coupling devices were aligned such that the spinal rod could be passed therethrough without distorting the screws. Because of such difficulty, polyaxial screw and coupling devices have been developed that allow limited movement of the coupling device relative to the implanted screw. Once a desired position is achieved, the coupling device is fixed relative to the screw.

However, while the prior art is replete with polyaxial screw and coupling devices for spine fixation systems, they only permit a limited freedom of movement with respect to angulation of the screw and the coupling device. Moreover, these prior art polyaxial screw and coupling devices are generally complex, inadequately reliable, and lack long-term durability. Furthermore, these prior art polyaxial screw and coupling devices do not allow the independent fixation of screw to coupling device angulation and rod fixation. These considerable drawbacks associated with prior art systems also include difficulty properly positioning the rod and coupling devices, and the tedious manipulation of the many small parts in the operation environment.

In view of the above, it is therefore an object of the present invention to provide a pedicle screw and rod coupling device assembly that provides polyaxial freedom of screw implantation angulation with respect to rod reception.

It is also an object of the present invention to provide a pedicle screw construct that provides independent fixation of angulation of the rod coupling device relative to the pedicle screw and of the spinal rod to the rod coupling device.

It is further an object of the present invention to provide a pedicle screw construct that provides angular reception of the spinal rod by the rod coupling device.

Accordingly, it is also an object of the present invention to provide a pedicle screw construct and/or spinal rod fixation assembly that is reliable, durable and which gives long term spinal fixation support.

These needs and/or objects, and others are accomplished through application of the principles of the subject invention and/or as embodied in one or more various forms and/or structures such as are shown and/or described herein.

SUMMARY OF THE INVENTION

The present invention provides various embodiments of a pedicle screw construct and/or a coupling construct for a pedicle screw for coupling a spinal rod relative to the pedicle screw. The pedicle screw construct may be part of a spine fixation system consisting of one or more connecting rods and one or more pedicle screw constructs. Adjunctive components, not forming a part of the subject invention, may be added such as cross members (that link parallel systems together), hooks and/or the like.

In one form, a coupling construct provides fixation of angular orientation of the coupling construct relative to the pedicle screw independent of the fixation of a spinal rod to the coupling construct. A pedicle screw construct including the present coupling construct forms one component or element in a spinal fixation system. The independent fixation coupling construct also provides for fixation of the angular orientation of the coupling construct while the coupling construct has received the spinal rod.

In one form, a coupling construct allows a pedicle screw shaft to pass therethrough but retain the pedicle screw head for rotation of the coupling head about the pedicle screw head and allow at least a 45° arc of pedicle screw shaft articulation relative thereto, such as to and about a longitudinal axis of a spinal rod received in the body.

The coupling construct is utilized on a pedicles screw to form a pedicle screw construct along with other components that allows articulation in a superior/inferior (head/toe) direction and a medial/lateral (side/side) direction.

In one particular form, there is provided a pedicle screw coupling device for holding a spinal rod relative to a pedicle screw. The pedicle screw coupling device includes a coupling head, a tubular sleeve, a collar and a spinal rod retention element. The head has a bore defining a first end sized to receive a pedicle screw shaft and a pedicle screw head of a pedicle screw, and a second end sized to allow the pedicle screw shaft to pass through but rotatably retain the pedicle screw head. The coupling head further includes a channel configured for reception of a spinal rod. The tubular sleeve is configured for reception in the coupling head bore and has a first and second end, the first end configured to abut the pedicle screw head. The collar is configured for releasable fixation onto the coupling head and to abut the second end of the tubular sleeve to apply pressure onto the pedicle screw head through the first end of the tubular sleeve to fix an orientation of the coupling head relative to the pedicle screw head. The spinal rod retention element is configured to be received through the collar and to fix a spinal rod received in the spinal rod channel of the coupling head relative to the coupling head, the fixation of the spinal rod relative to the coupling head independent of the fixation of the coupling head relative to the pedicle screw head.

In another particular form, there is provided a pedicle screw coupling head for holding a spinal rod relative to a pedicle screw having pedicle screw head and a pedicle screw shaft. The pedicle screw coupling head includes a body, a channel formed in the body and configured to receive a spinal rod, and a pedicle screw bore formed in the body and having a first end sized to receive a pedicle screw shaft and a pedicle screw head of a pedicle screw and a second end sized to allow the pedicle screw shaft to pass through but retain the pedicle screw head, the second end configured to allow rotation of the coupling head about the pedicle screw head and to allow the body to pivot relative to the pedicle screw shaft in an arc perpendicular to a longitudinal axis of a spinal rod received in the channel, the arc defining a length of travel of substantially −5° to substantially +45° relative to an axis defined by the pedicle screw shaft.

In another particular form, there is provided a method of fixing a spinal rod relative to a pedicle screw in a spine fixation system. The method includes the steps of: (a) providing a pedicle screw coupling device having a body, a channel formed in the body and configured to receive a spinal rod, a pedicle screw bore formed in the body and having a first end sized to receive a pedicle screw shaft and a pedicle screw head of a pedicle screw and a second end sized to allow the pedicle screw shaft to pass through but retain the pedicle screw head, the second end configured to allow rotation of the coupling head about the pedicle screw head and to allow the body to pivot relative to the pedicle screw shaft in an arc perpendicular to a longitudinal axis of a spinal rod received in the channel, the arc defining a length of travel of substantially −5° to substantially +45° relative to an axis defined by the pedicle screw shaft; (b) attaching the pedicle screw coupling device to a pedicle screw; (c) inserting a spinal rod into the spinal rod channel; and (d) fixing an arcuate orientation of the coupling device relative to the pedicle screw.

BRIEF DESCRIPTION OF THE DRAWINGS

The above mentioned and other features and objects of this invention, and the manner of attaining them, will become more apparent and the inventions will be better understood by reference to the following description of embodiments of the invention taken in conjunction with the accompanying drawings, wherein.

Figure 1:
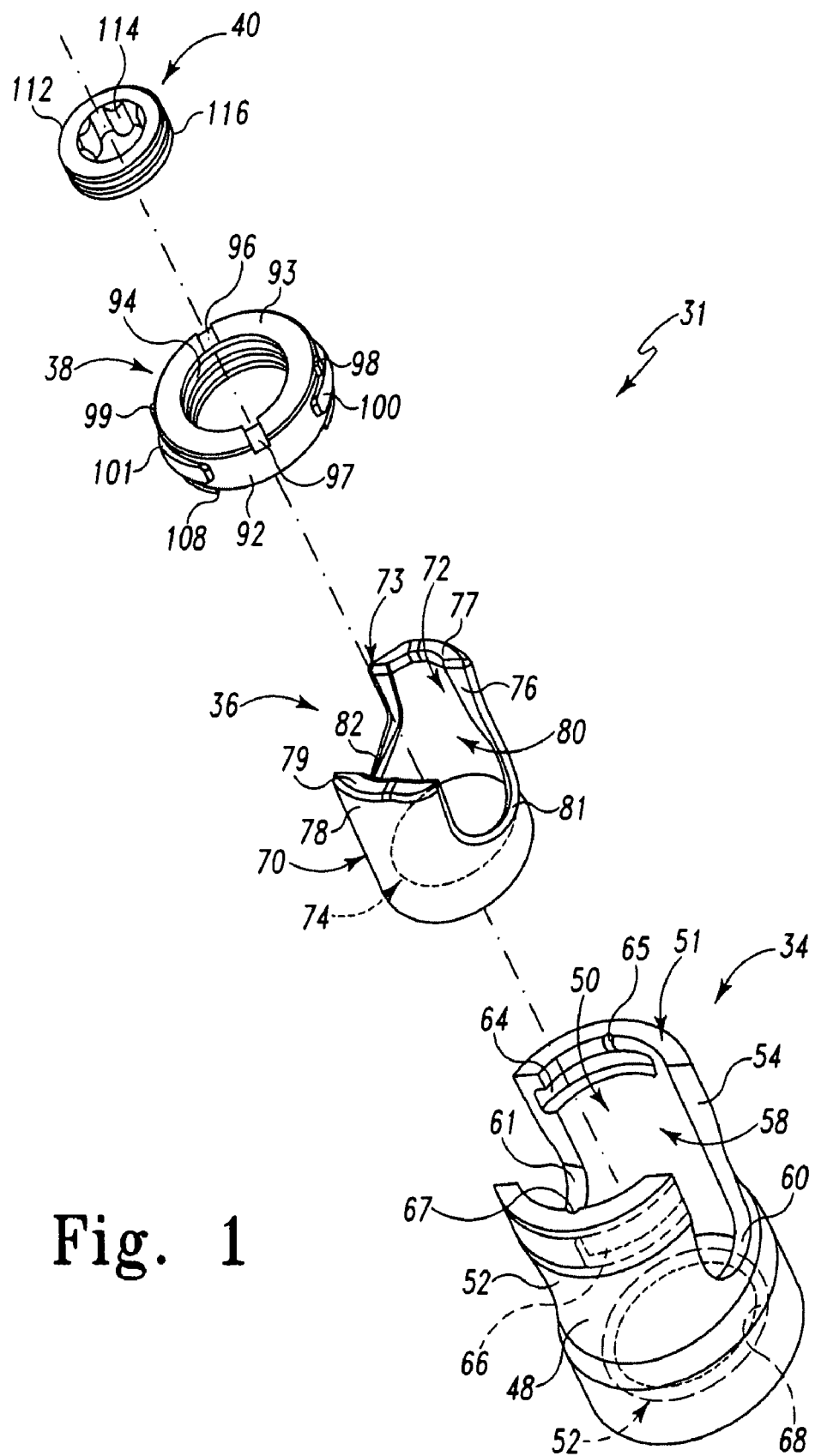
FIG. 1 is an exploded perspective view of a pedicle screw construct in accordance with the present principles for holding a spinal rod relative to a pedicle screw in a spine fixation system.

Corresponding reference characters indicate corresponding parts throughout the several views. Although the drawings represent various embodiments of the invention, the drawings are not necessarily to scale and certain features may be exaggerated in order to better illustrate and explain the invention. Also, the exemplifications set out herein illustrate various embodiments of the invention, but such exemplifications are not to be construed as limiting the scope of the invention in any manner.

DETAILED DESCRIPTION OF THE INVENTION

Referring to FIG. 1, there is depicted an exploded view of an embodiment of a spinal rod fixation device, construct or assembly, generally designated 30. The spinal rod fixation device 30 is used as a component in a spinal rod type spine fixation system or assembly. Particularly, the spinal rod fixation device 30, consisting of a coupling device, construct or assembly 31 and a pedicle screw 32, is used to attach or fix a section of a spinal rod (not shown) of the spine fixation assembly relative to a vertebrae of the spine. More particularly, the pedicle screw 32 is configured, adapted and/or operable to be attached to a vertebra in a known manner, while the coupling construct 31 receives and fixes, retains or holds the section of the spinal rod (the spinal rod is fixed to the coupling construct). The coupling construct 31 is movably positionable relative to the pedicle screw 32 as further described herein. The coupling construct 31 may also be termed a pedicle screw construct, pedicle screw coupling device, or the like.

The coupling construct 31 includes a head 34, a sleeve 36, a collar 38 and a fixation element 40. The head 34 is configured, adapted and/or operable for reception and retention onto the head 42 of the pedicle screw 32 and to be fixedly, but releasably, angularly oriented with respect to a longitudinal axis of the pedicle screw 32 (e.g. the shank 42 of the pedicle screw 32). The head 34 is further configured, adapted and/or operable for releasable retention or holding of a spinal rod. The coupling construct 31 is received onto the pedicle screw head 44 and is releasably fixable (positioned) relative thereto within a range of angular orientations. In accordance with an aspect of the subject invention, the fixing, retaining or holding of the spinal rod to the coupling device 31 does not fix the angular orientation of the coupling device 31 relative to the pedicle screw head 44. Rather, as explained further below, the angular orientation of the head 34 and pedicle screw 32 is releasably fixed independent of the releasable affixation of the spinal rod to the head 34. Thus, in one manner of implanting, the angular orientation of the head relative to the pedicle screw is selected and fixed while the spinal rod is received in the head but not fixed thereto. The spinal rod is then releasably affixed to the head after the angular positioning of the head/pedicle screw.

The head 34 of the coupling construct 31 is characterized by a body 48 having an axial bore 50 therethrough that defines a first end or opening 51 and a second end or opening 52. The body 48 is generally cylindrical or tubular shaped with a slight narrowing on the middle outside of the body 48. The bore 50 is sized such that at the first end 51, a pedicle screw shank and head may easily pass. The bore 50 is sized such that at the second end 52 the pedicle screw shank may pass, but the pedicle screw head will not. A radially inward slope 68 is provided at the second end 52 for capturing the pedicle screw head but allow for rotational and angular movement of the head 34 on the pedicle screw head. This allows the angular orientation of the head 34 to be changed relative to the pedicle screw A slot 58 is formed in the body 48 having an axis that is essentially perpendicular to the bore 50. The slot 58 extends through both sides of the body 48 to define a generally U-shaped channel therebetween and a seat or seating surface 60 on one side of the body 48 and a seat or seating surface 61 on another side of the body 48. The slot 58 is sized to receive a spinal rod. The spinal rod is retained against the seats 60, 61 when affixed to the head 34 as described herein. The bore 50 and slot 58 define first and second walls 52 and 54 that extend from the end 52. The walls 52 and 54 are generally arcuate shaped and have a height sufficient to extend over a spinal rod and receive the collar 38 and the fixation device 40.

The inside of each wall 52 and 54 includes a respective groove or slot 64 and 66. Each slot 64, 66 extends or begins (provides an opening) at opposite (180°) sides of the respective wall 52, 54 and extends a radial distance about the wall 52, 54. Preferably, the slots 64, 66 do not extend to the other side of the respective wall 52, 54. Each slot is adapted to receive a flange of the collar 38. In addition, the body 48 includes first notch 65 on the inside periphery of the wall 54, and a second notch 67 on the insider periphery of the wall 52. The notches 65, 67 are sized and/or configured to receive a detent of the collar 38. These features allow the collar 38 to be received and rotated into a snap fit retained or locked position relative to the head 34.

The sleeve 36 or taper lock element of the coupling construct 31 is adapted, configured and/or operable to be received in the head 34 and to interact with the pedicle screw head and collar 38 for providing fixation of an angular orientation or position of the head 34 (coupling construct 31) relative to or with respect to the associated pedicle screw. The sleeve 36 is characterized by a body 70 having an axial bore 72 therethrough that defines a first end or opening 73 and a second end or opening 74. The body 70 is generally cylindrical or tubular shaped. A slot 80 is formed in the body 70 having an axis that is essentially perpendicular to the bore 72. The slot 80 extends through both sides of the body 70 to define a generally U-shaped channel therebetween and a seat or seating surface 81 on one side of the body 70 and a seat or seating surface 82 on another side of the body 70. The slot 80 is sized to receive a spinal rod. The spinal rod is retained against the seats 81, 82 when affixed to the coupling construct 31 as described herein. The bore 72 and slot 80 define first and second walls 76 and 78 that extend from the end 74. The walls 76 and 78 are generally arcuate shaped and have a height sufficient to extend over a spinal rod and be abutted by the collar 38 during angular position fixation of the coupling construct 31 to the pedicle screw.

Figure 2:
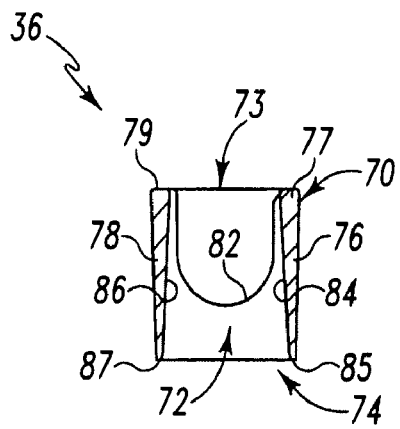
FIG. 2 is a sectional view of the locking sleeve of the pedicle screw construct of FIG. 1.
Figure 4:
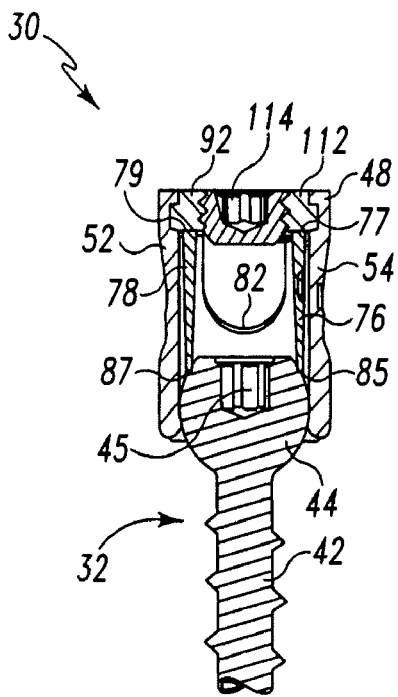
FIG. 4 is a sectional view of the pedicle screw construct of FIG. 1 assembled onto the pedicle screw, taken along line 4-4 thereof.
Figure 5:
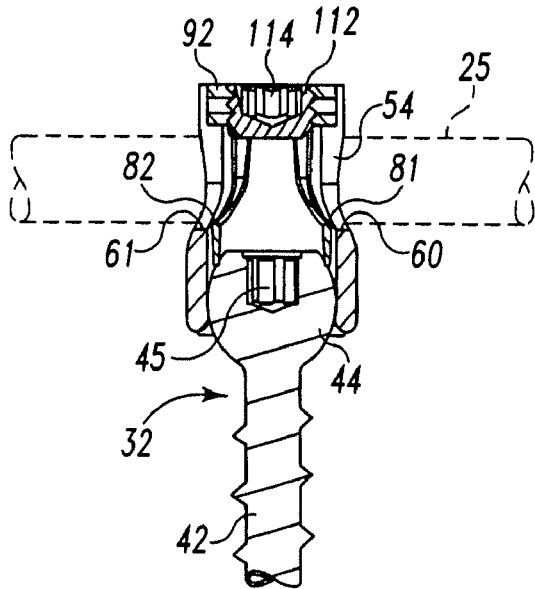
FIG. 5 is another sectional view of the pedicle screw construct of FIG. 1 assembled onto the pedicle screw, taken along line 3-3 thereof.

Referring additionally to FIG. 2, a sectional view of the sleeve 36 is shown. The bore 72 is defined in the body 70 such that the inner side wall 84 of the wall 76 is angled or tapered as is the inner side wall 86 of the wall 78. The upper ends 77 and 79 of the end 73 (walls 76 and 78) are thus thicker than the ends 85 and 87 of the end 74 (walls 76 and 78). Thus, when pressure is applied to the end 73, the end 74 will tend to spread or flare radially outward. As best seen in FIGS. 4 and 5, pressure and this process fixes or wedges the construct 31 relative to the screw 32.

The collar 38 of the coupling construct 31 is adapted, configured and/or operable to be releasably lockingly received in the head 34 and provide a means or manner in which the angular position or orientation of the coupling construct 31 relative to the pedicle screw on which it is coupled. The collar 38 has a body 92 of a generally annular or ring shape. The body 92 defines a first or upper annular side or surface 93. The inner surface 94 of the annular body 92 is threaded to receive a like threaded component or element (e.g. the fixation element 40). Two cutouts or notches 96 and 97 are provided in surface 93 that are sized to receive an insertion tool for rotating the collar 38 into position relative to the head 34.

For this purpose the body 92 includes two elongated flanges 100, 101 disposed on the annular outer periphery of the body 92, preferably opposite one another. The flanges 100, 101 are sized to be received in slots 64 and 66 of the head and are thus configured and/or sized accordingly. Moreover, two detents 98 and 99 are disposed on the upper rim of the surface 93. The detents 98, 99 are sized to be received in the notches 65, 67 of the head when the collar 38 is rotatably received in the head 34.

Figure 3:
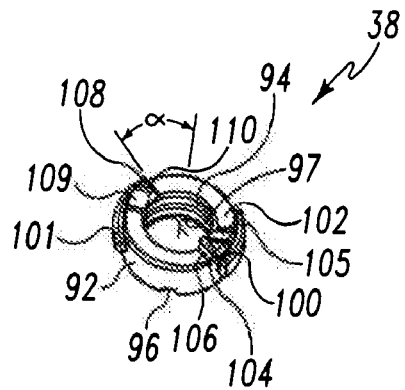
FIG. 3 is a bottom view of the retaining collar of the pedicle screw construct of FIG. 1.

Referring additionally to FIG. 3, the annular or ring shaped lower end or surface 102 of the body 92 is shown. The lower surface 102 contacts the sleeve for compression against the pedicle screw head. The lower surface 102 has a first detent structure 104 having a ramped portion 105 and defining a stop surface 106, and a second detent structure 108 having a ramped portion 109 and defining a stop surface 110. The detent structures 104, 108 are positioned at an angle $\alpha$ with respect to a centerline, and adjacent a beginning of a flange 100, 101. Thus, the detent structures 104, 108 line up with the rod slot 58 of the head 34 but are rotated into pressure engagement with the upper surface 77, 79 of the sleeve 36. This is best illustrated in FIGS. 4 and 5 which show cross sectional views of the coupling construct 31 on the pedicle screw 32.

The fixation element 40 of the coupling construct 31 is adapted, configured and/or operable to releasably fix a spinal rod to the coupling construct 31 and is received in the threaded opening 94 of the collar 38. As such, the fixation element or set screw 40 has a generally annular body 112 having external threads 116 on the outer annular periphery thereof. Additionally, the body 112 includes a configured bore 114 for receiving an insertion tool. Insertion of the fixation element 40 into the collar 38 presses and fixes the spinal rod to the coupling construct 31 independent of the fixation of the orientation of the coupling construct 31 relative to the pedicle screw 32. Again, this is best illustrated in FIGS. 4 and 5.

Referring specifically to FIGS. 4 and 5, the manner in which the coupling construct 31 is received on a pedicle screw head 44, receives a spinal rod 25 (shown in dashed line), and allows fixation of the angular orientation of the coupling construct 31 relative to the pedicle screw 32 independent of the fixation of the spinal rod 25 to the coupling construct 31 is best seen. FIG. 4 shows that the collar body 92, when inserted into the head 34, provides downward pressure on the upper ends 77, 79 of the sleeve walls 76, 78. The downward pressure is transmitted to lower ends 85, 87 that spread slightly due to its taper to bind against the pedicle screw head 44. Of course, removal of the collar body 92, relieves pressure on the pedicle screw head 44 to allow angular positioning of the coupling construct 31 relative thereto. FIG. 5 shows the receipt of the spinal rod 25 within the channels 58 and 80 of the head 34 and the sleeve 36 respectively. The rod 25 rests upon the seats 60, 61 of the head 34 and the seats 81, 82 of the sleeve 36. The seats 60, 61, 81, 82 hold the rod 25 above the pedicle screw head 44. The fixation elements 40 (e.g. set screw) is threadedly received in the threaded bore of the collar body 92. The set screw 40 provides pressure against the rod 25 to fix the rod 25 relative to the coupling construct 31 independent of the coupling head/pedicle screw fixation.

Figure 6:
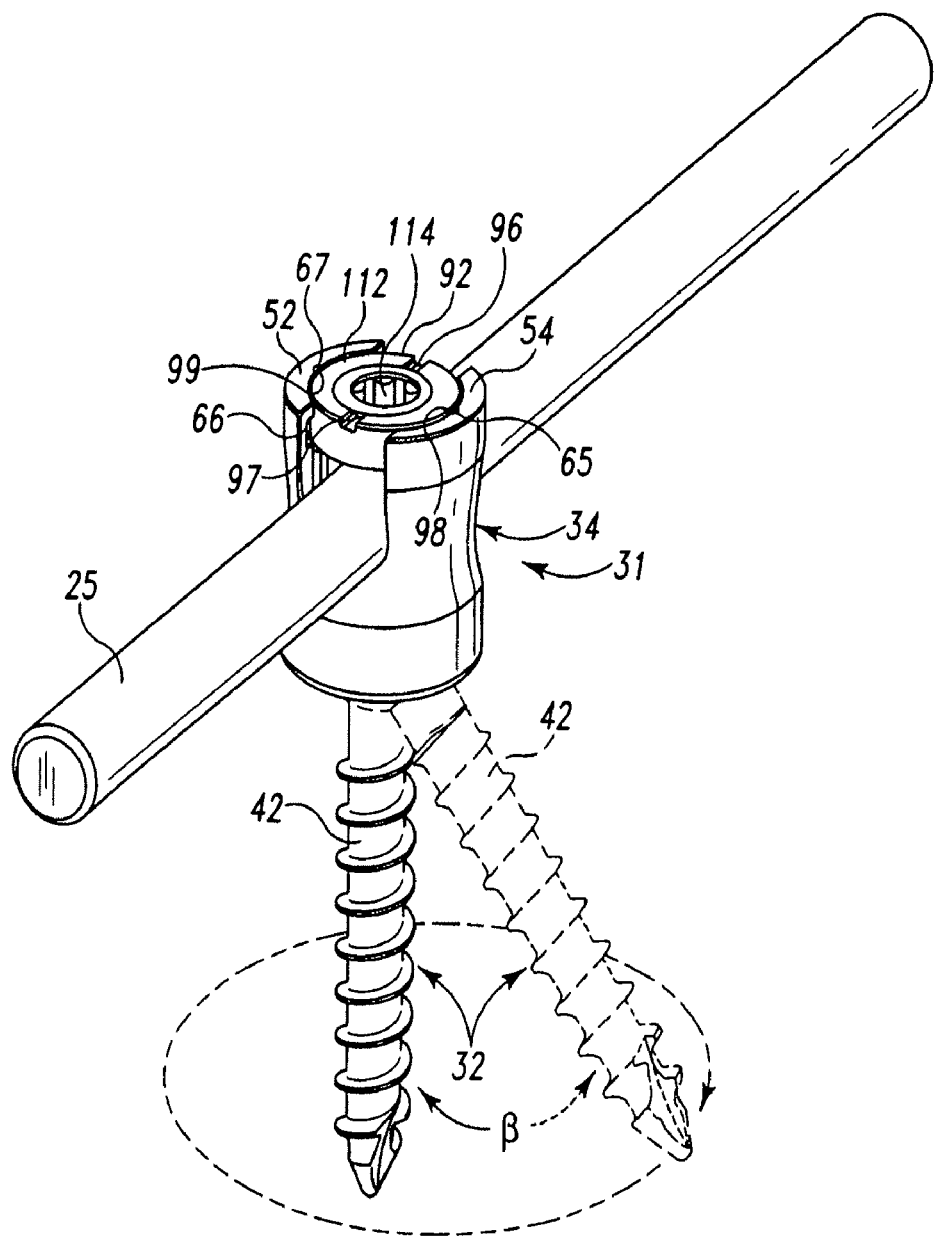
FIG. 6 is a perspective view of the pedicle screw construct of FIG. 1 assembled onto a pedicle screw and holding a spinal rod relative thereto, the pedicle screw illustrated in two positions relative to the head of the pedicle screw construct illustrating the limits of the range of angular orientations of the pedicle screw relative to the head of the pedicle screw construct.

FIG. 6 shows an assembled coupling construct 31 retaining the spinal rod 25 and illustrating the various angular positions or orientations possible between the coupling construct 31 and the pedicle screw 32. The orientation of the pedicle screw 32 is shown in various positions relative to the coupling construct 31 for ease of illustration. The coupling construct 31 is infinitely variable from 0° (i.e. a vertical axis of the coupling construct 31 coaxial with a longitudinal axis of the screw 32 or shaft 42 thereof) up to about 90° (i.e. at an angle $\beta$ of about 45°±2° from the vertically aligned screw shaft axis and the coupling construct 31).

Figure 7:
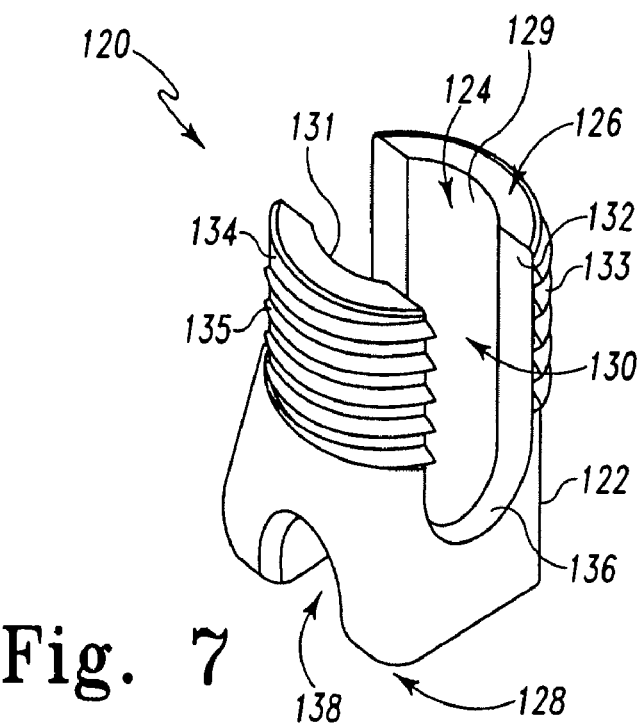
FIG. 7 is a perspective view of another embodiment of a head for a pedicle screw construct in accordance with the principles of the subject invention.
Figure 8:
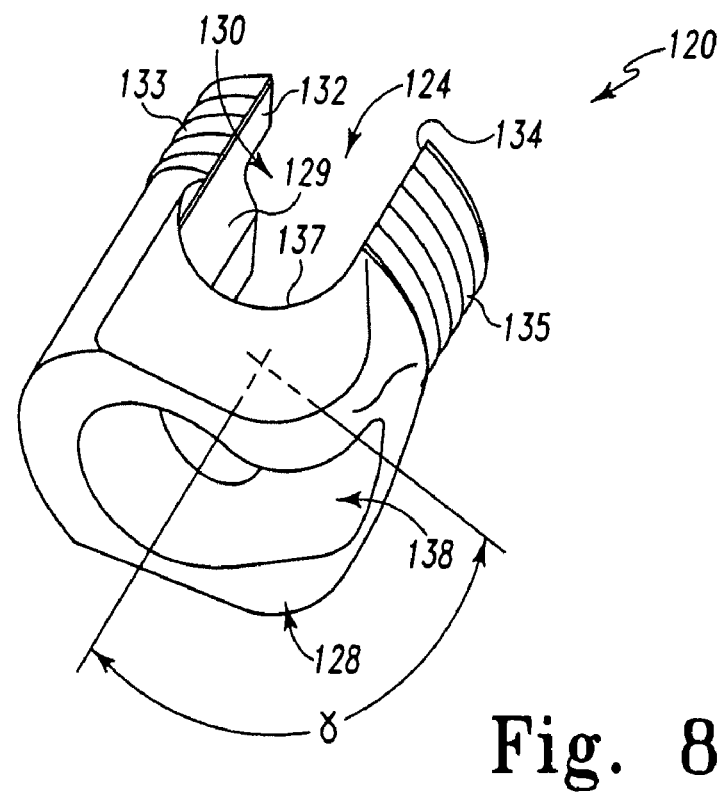
FIG. 8 is a perspective view of the pedicle screw construct head of FIG. 5 relative to a pedicle screw illustrating the limits of the range of angular orientations of the pedicle screw relative to the pedicle screw construct head.

Referring now to FIGS. 7 and 8, there is depicted two views of another exemplary embodiment of a head or coupling member/element for a spine fixation coupling construct that is generally designated 120. The head 120 is fabricated from a suitable surgical material such as a metal, metal alloy, polymer or the like as is the other heads and/or components of the present invention. The coupling member 120 is characterized by a body 122 that, in one side profile defines a snub toed boot or shoe shape. This, along with an enlarged pedicle screw head reception area or channel 138 allows the construct to rotate approximately −10° (± a few degrees) to approximately 90° (± a few degrees) in one or more planes.

The body 122 has a central bore 124 defining a first end 126 and a second end 128. The first end 126 receives a pedicle screw (shank end first) while the second end 128 allows the pedicle screw shank to extend therethrough, but swivelbly retain or hold the pedicle screw head in like manner to the head 34 of the pedicle screw construct 31. The bore 124 defines a first wall 132 extending from a lower portion of the body 122 and a second wall 134 extending from the lower portion of the body 122. The walls 132 and 134 are arcuate and preferably, but not necessarily, formed as portions of a circle. The respective outer surface of each wall 132, 134 includes respective threading 133, 135, while the respective inner surface of each wall 132, 134 includes respective elongated, arcuate channels 129, 131. The walls 132, 134 are shaped to form a U-shaped channel 130 therethrough. The channel 130 is sized to receive a spinal rod therein. Moreover, the channel 130 defines seats 136, 137 that support the spinal rod.

As best seen in FIG. 8, the pedicle screw head retention end 128 of the head 120 includes a cutout portion or notch 138 that intersects with the bore 124 to create a slot, channel, groove or the like at the end 128. The configured channel 138 allows the shank of a pedicle screw to swivel through an angle $\gamma$ defined as between a longitudinal axis of the bore 124 and a perpendicular thereto. Thus, the head 120 is releasably positionable on the pedicle screw head from 0° (wherein the bore 124 is coaxial with the pedicle screw shaft, such as is depicted in FIG. 2) to approximately 90° (wherein the pedicle screw shaft axis is perpendicular to the axis of the bore 124). Of course, the head 120 may rotate about the pedicle screw head in an unrestricted manner (360°) regardless of the position of the pedicle screw shaft relative to the axis of the bore 124. Particularly, the end 128 (including slot 138) allows the capture of the screw head such that the coupling member 120 may rotate 360° about the head of the bone screw. Particularly, the slot 138 allows the articulation of the bone screw from an approximately a −10° (± a few degrees) position (where a longitudinal axis of the coupling member 120 is coaxial with a longitudinal axis of the bone screw shaft), to a +90° (± a few degrees) position and to all continuous angles therebetween.

Figure 9:
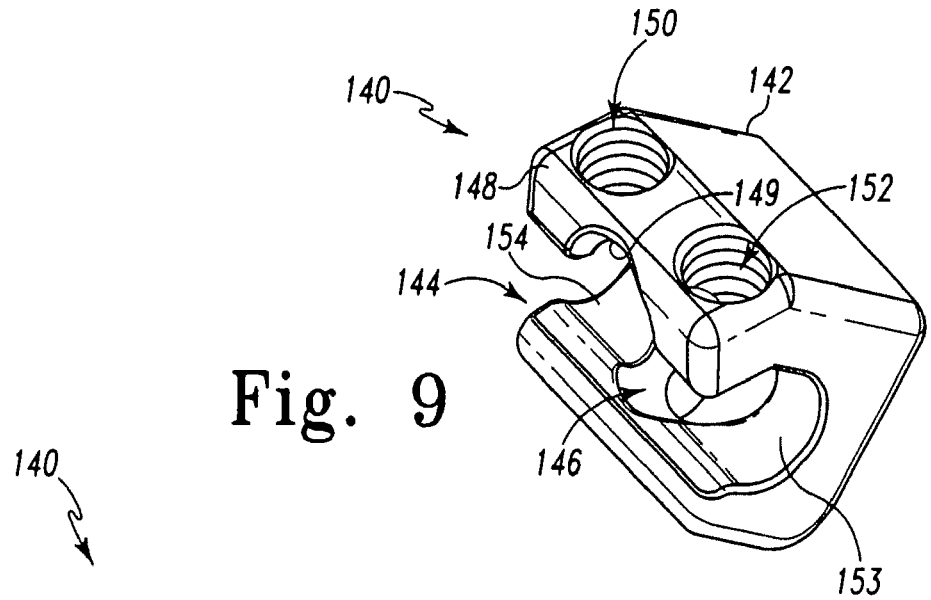
FIG. 9 is a top perspective view of another embodiment of a head for a pedicle screw construct in accordance with the principles of the subject invention.
Figure 10:
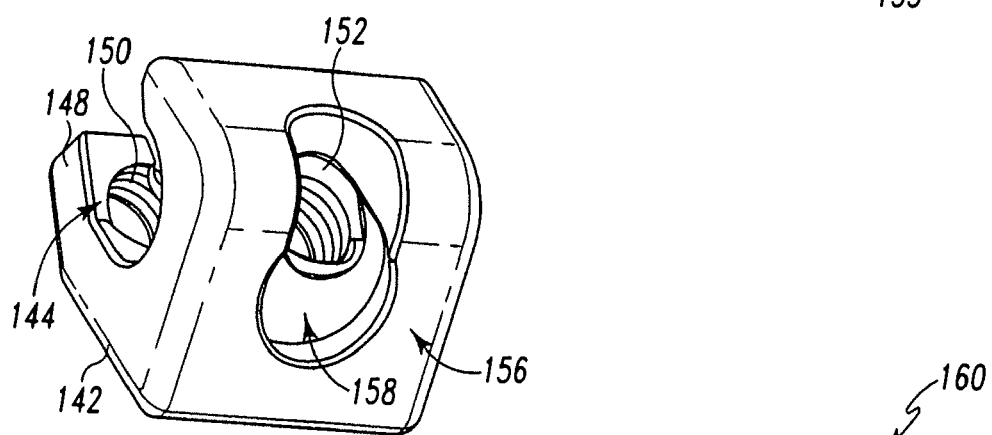
FIG. 10 is a bottom perspective view of the pedicle screw construct head of FIG. 9.

Referring to FIGS. 9 and 10 there is shown two perspective views of an alternative embodiment of a coupling member or head generally designated 140. The coupling head 140 retains the ability to allow movement between it and a bone screw in like manner as the coupling head 120 of FIGS. 7 and 8. The coupling member 140, however, incorporates features not present in the coupling member 120 of FIGS. 7 and 8.

The coupling member 140 has a body 142 that is formed in a generally block rectangular shape, particularly with respect to a longitudinal axis transverse to a bone screw attached thereto and in a 0° orientation. The body 142 may take on different forms consistent with the principles of the subject invention. The body 142 defines an elongated channel 144 that is sized to receive a length of a spinal fixation rod. The rod channel 144 defines rod seats 153, 154. Moreover, the rod channel 144 is slightly enclosed by an arched portion 148 of the body 142. The arched portion 148 axially extends over a bone screw bore 146 in the body 142 and includes a cutout portion 149 to allow for the insertion of a collar (see, e.g. FIG. 11) and/or a bone screw. At least one, and shown here as two, set screw or rod fixation element bores 150 and 152 are disposed in the arched portion 148. The side loads the spinal rod for releasable fixation of the spinal rod to the head 140. Each bore 150, 152 is threaded to receive a threaded set screw (see e.g. element 40 of FIG. 1) that releasably retains or affixes the fixation rod therein once the fixation rod is in a proper position. The arched portion 148 provides an angled or side mount (rather than from the top) for receipt of the spinal rod. The opening of head 140 is at an approximately 45° offset.

The bottom 156 of the head 140 includes a slot 158 in communication with the bore 146 and configured in like manner to the slot 138 of head 120. This allows the same freedom of movement for variable angular positioning of the head 120 relative to a received pedicle screw. The opening 158 is tapered to retain the rounded head of a bone screw and/or collar from exiting from the coupling member 140.

Figure 11:
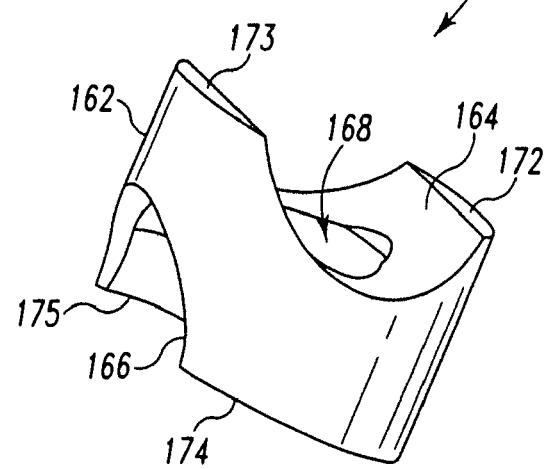
FIG. 11 is a perspective view of a holding collar for a pedicle screw construct utilizing the pedicle screw construct head of FIGS. 9 and 10.

Referring to FIG. 11, an exemplary embodiment of a collar, generally designated 160, that may, and preferably but not necessarily is, utilized with the coupling head 140. The collar 160 is characterized by a body 162 having a configured bore 168 along an axis of the cylindrical body 162. A first concave surface 164 is provided at one end of the body 162 and is shaped as a portion of a cylinder that has a longitudinal axis that is transverse to the axis of the body 162 (and/or bore 168). The concave surface 164 defines first and second ends 172, 173.

A second concave surface 166 is provided at another end of the generally cylindrical or tubular body 162 opposite the first concave surface 164. The second concave surface 166 is likewise shaped as a portion of a cylinder that has a longitudinal axis that is transverse to the axis of the body 162 (and/or bore 168). The concave surface 166 defines first and second ends 174, 175. The first and second concave surfaces 164 and 166, however, are disposed at essentially right angles to each other while the ends 172, 173 and 174, 175 are opposite one another. The first and second concave surfaces 164, 166 provide an hourglass configuration to the collar 160 in cross section. The first and second concave surfaces 164, 166 respectively receive the head of a bone screw and a fixation rod for applying a fixation pressure from the rod to the screw.

Figure 12:
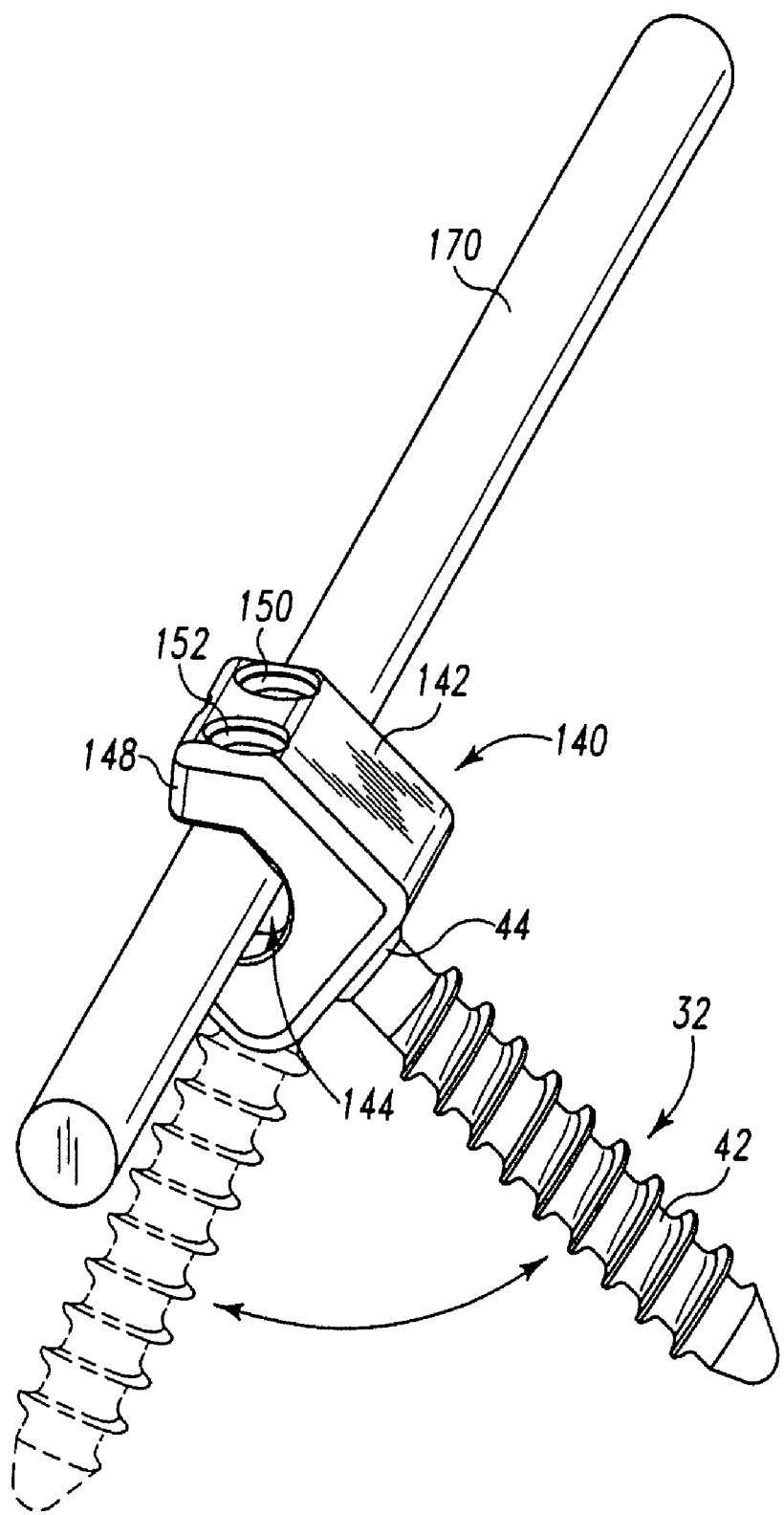
FIG. 12 is a perspective view of a pedicle screw construct utilizing the head of FIGS. 9 and 10 along with the collar of FIG. 11 assembled onto a pedicle screw and holding a spinal rod.

Referring to FIG. 12 there is depicted an exemplary embodiment of a spine fixation construct, utilizing a pedicle screw 32 and the coupling head 140, holding a spinal rod 170. The pedicle screw 32 is positioned in a 0° position as one limit of its pivoting range and shown in dashed lines in a 90° position as the other limit of its pivoting range. It should be appreciated, however, that the coupling member 140 may be positioned in the various manners as described for the construct of FIG. 6. Not shown, are set screws that would be inserted into the set screw bores 150, 152 of the body 142 in order to fix the longitudinal positioning of the spinal rod 170. Likewise, the collar 160 is not shown.

Figure 13:
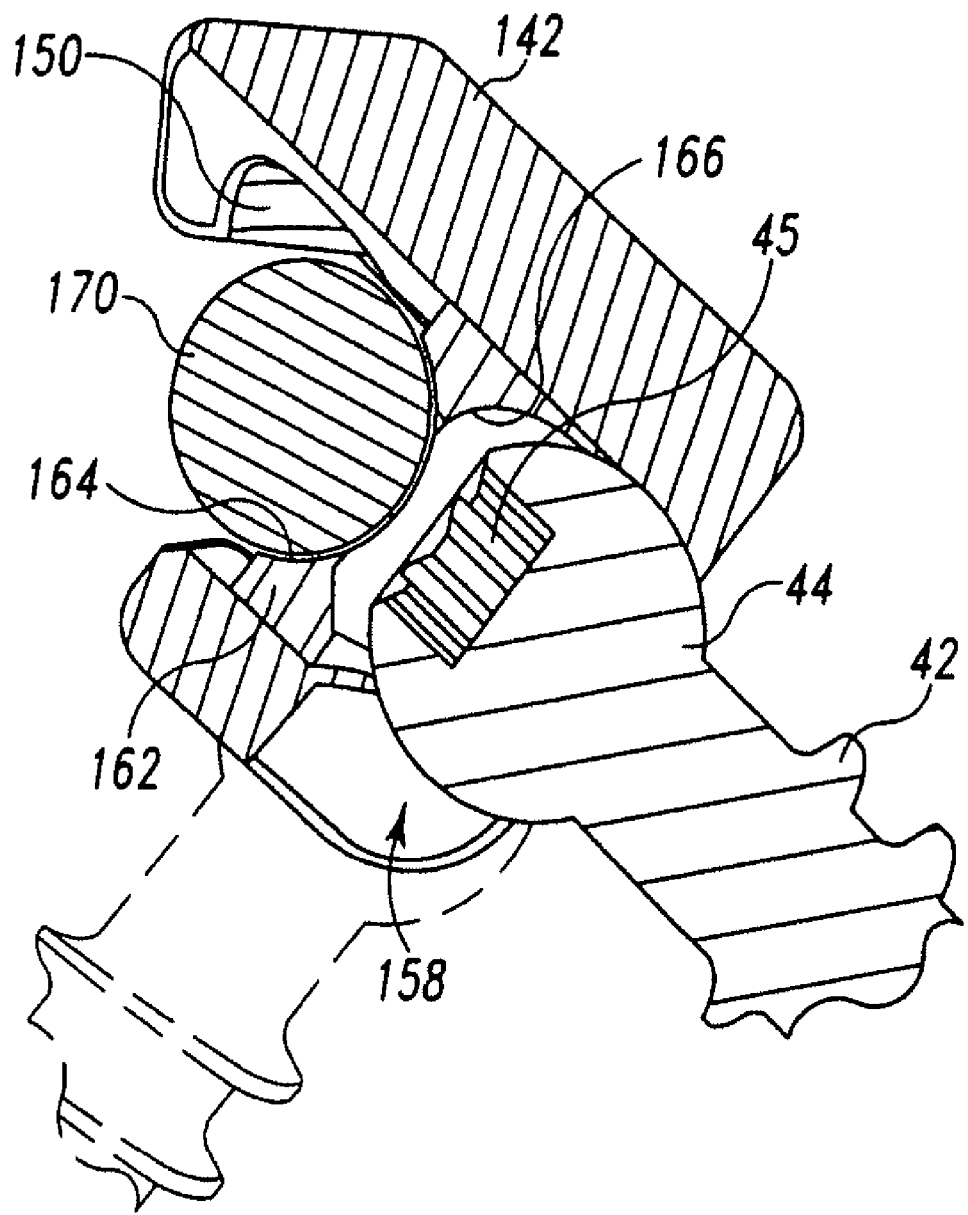
FIG. 13 is an enlarged portion of the pedicle screw assembly of FIG. 12 in sectional view.

FIG. 13 depicts a side sectional view of the construct of FIG. 12, particularly taken along the axis of the pedicle screw shaft 42. The spinal rod 170 rests against the surface 164 of the collar body 162 while the pedicle screw head 44 is disposed adjacent the surface and contacted by the sides thereof. Loading of the spinal rod 170 by set screws (not shown) through the set screw bores 150, 152 results in pressure upon the collar 166 which forces against the pedicle screw head 44 thereby fixing its position relative to the coupling head 142. Thus, the depiction of FIG. 13 illustrates the cooperation and/or interaction of the rod 170, the collar 160 and the head 44 of the screw 32. It should be appreciated that the various components are not necessarily sized accordingly. As connecting rod 170 is urged downwardly into the socket of the collar body 162 by set screws (not shown) extending through the set screw bores 150, 152, the socket collar body presses against the head 44 of the screw 32. This creates a friction fit to lock the orientation of the coupling head 140 relative to the rod 170 and the screw 32.

Figures 14, 15:
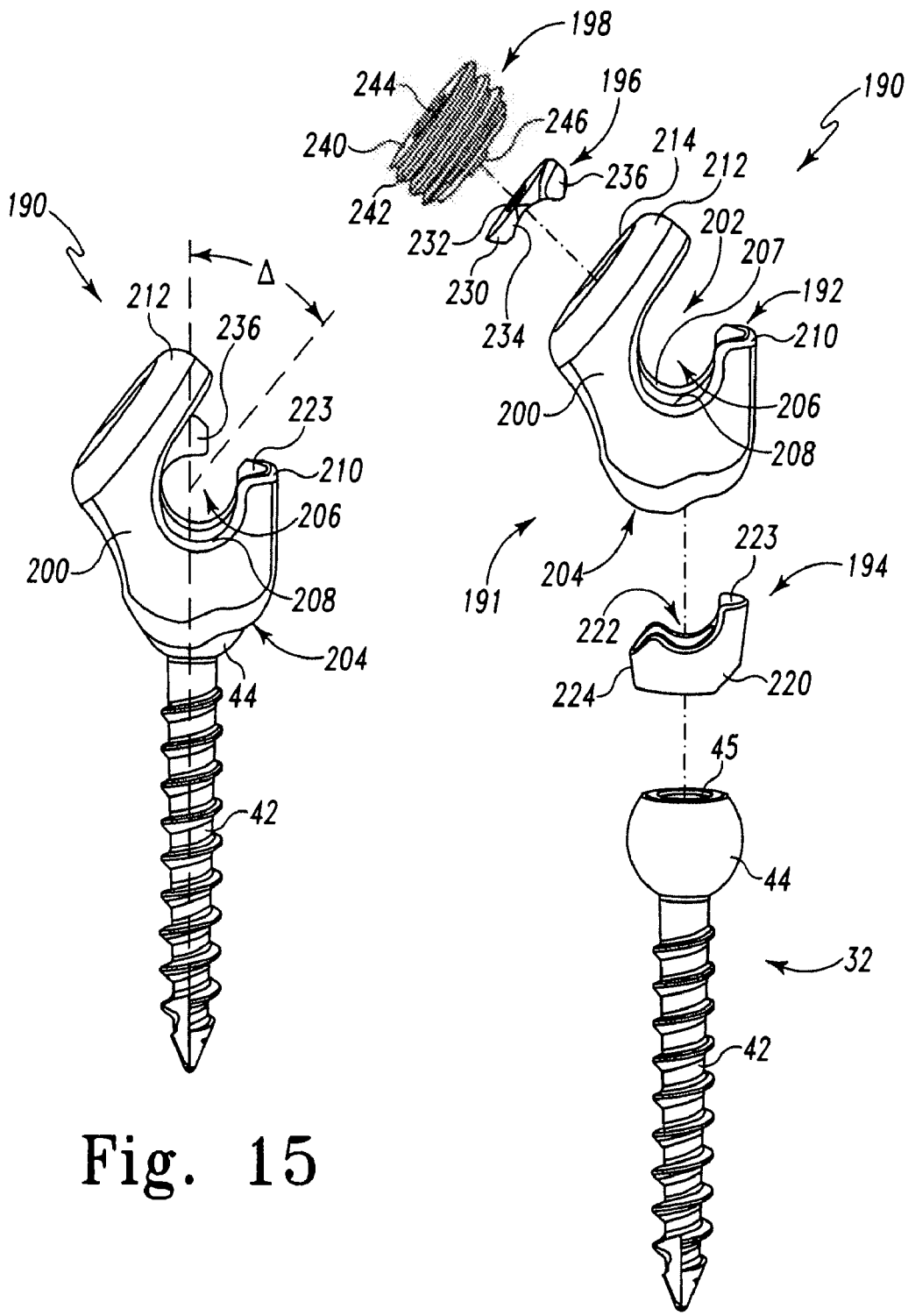
FIG. 14 is an exploded perspective view of another embodiment of a pedicle screw construct in accordance with the present principles for holding a spinal rod relative to a pedicle screw in a spine fixation system.
FIG. 15 is a side view of the pedicle screw construct of FIG. 14 assembled onto the pedicle screw.
Figure 18:
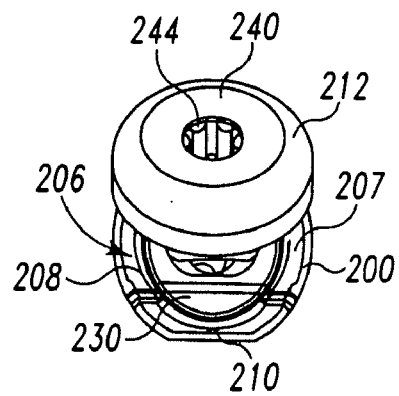
FIG. 18 is a top view of the assembled pedicle screw construct of FIG. 16.

Referring now to FIGS. 14-18, there is depicted various views of another pedicle screw construct 190 having a coupling construct 191 and a pedicle screw 32. FIG. 14 provides an exploded view of the pedicle screw construct 190 having a coupling construct 191 in exploded view for attachment onto the pedicle screw 32. The coupling construct 191 includes a head 192, a sleeve 194 that is received in the head 192, a rod retention element 196 that is received by the head 192, and a set screw or fixation element 198 that is also received by the head 192.

Figure 17:
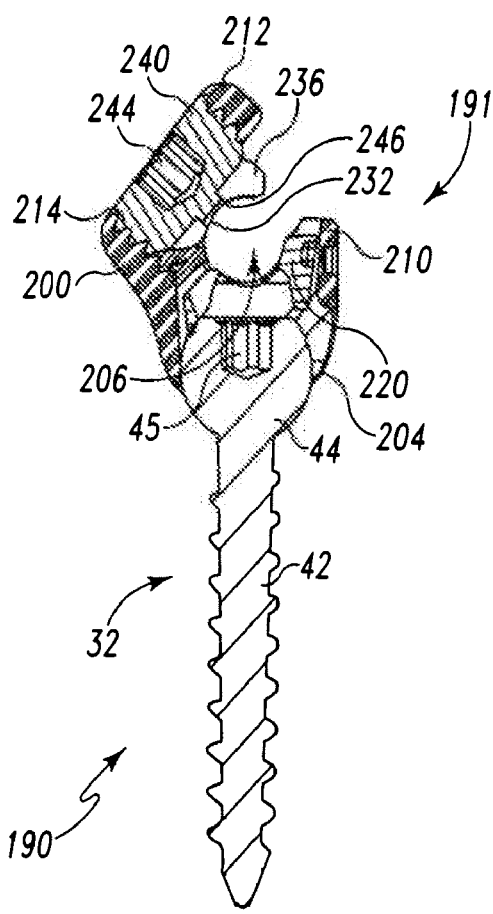
FIG. 17 is a sectional view of the assembled pedicle screw construct of FIG. 16 taken along line 17-17 thereof.
Figure 16:
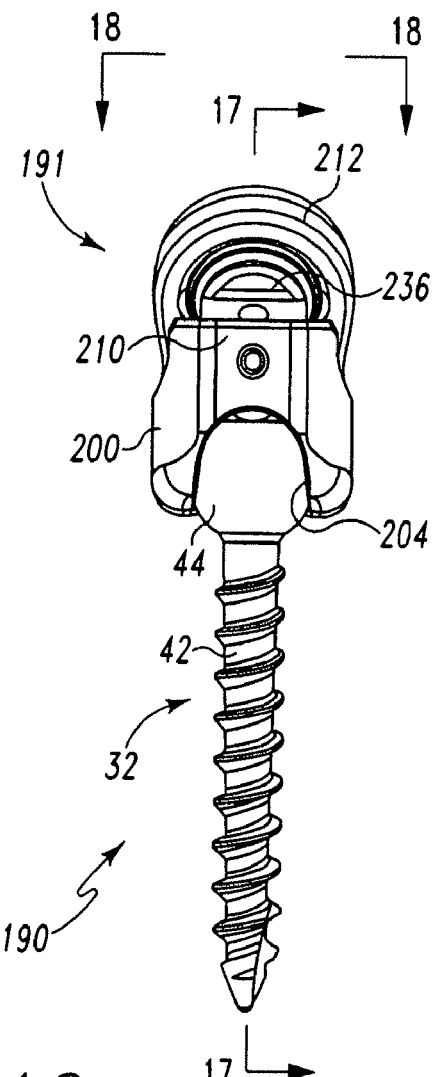
FIG. 16 is an end view of the pedicle screw construct of FIG. 14 assembled onto the pedicle screw.

The head 192 of the coupling construct 191 is characterized by a body 200 having a shape that melds at least some of the features of the various coupling heads of the present invention. Particularly, the body 200 has a bore 202 for reception of the pedicle screw 32 therethrough and extension of only the shaft 42 thereof through the configured end 204 of the body 200, the head 44 of the screw 32 being rotationally captured, retained or held by the configured end 204. The configured end, as best seen in FIGS. 16 and 17, is shaped or channeled in like manner to the channels 138 and 158 of the coupling heads 120 and 140. As such the head 192 provides the same rotation and swiveling range of motion as the heads 120 and 140. The body 200 further defines a spine rod channel 206 for reception of a spinal rod. Rod seats 207, 208 provide support for the rod against the head 192. The body also has a tilted or angled, generally annular top portion 212 having a threaded bore 214. The top portion 212 is angled to provide an angled inlet for a spinal rod into the rod channel 206. As best seen in FIG. 15, the top portion 212 creates a rod reception inlet that is angled ( ) relative to a 0° position. This provides angled loading against the rod by the rod retention element 198, whose nose 236 as seen in FIG. 15, cups around and retains a spinal rod.

The sleeve 194 of the coupling construct 191 has a generally cup-shaped body 224 with a saddle-shaped cavity 222 that defines a front side 224 and a rear side 223 having a shaped that mimics the front 210 of the body 200 of the head 192. As best seen in FIG. 17, the body 220 provides a seat for a spinal rod and a fixation element for the pedicle screw head 44. Thus, as a spine rod is loaded as described below, the sleeve 194 is loaded against the pedicle screw head 44 to fix the position of the construct 191 relative to the pedicle screw 32.

The rod retention element 196 of the coupling construct 191 is characterized by a body 230 having a generally flat top surface having a hole 232 therein. The body 230 also defines an arcuate portion 234 and a configured nose or protrusion 236. The nose 236 cradles the spinal rod when assembled.

The set screw or fixation element 198 of the coupling construct 191 is characterized by a generally annular or disk shaped body 240 having threading 242 on the external annular periphery of the body 240. The threading is sized to thread with the threaded bore 214 of the top portion 212 of the head 214 and thus to be inserted therein. The fixation element 198 further includes a configured socket 244 on a top surface thereof for driving the fixation element 198, and a boss 246 on a lower surface thereof. The boss 246 is sized to register with the bore 232 of the rod retention device 196 when assembled (see e.g. FIG. 17).

Figure 19:
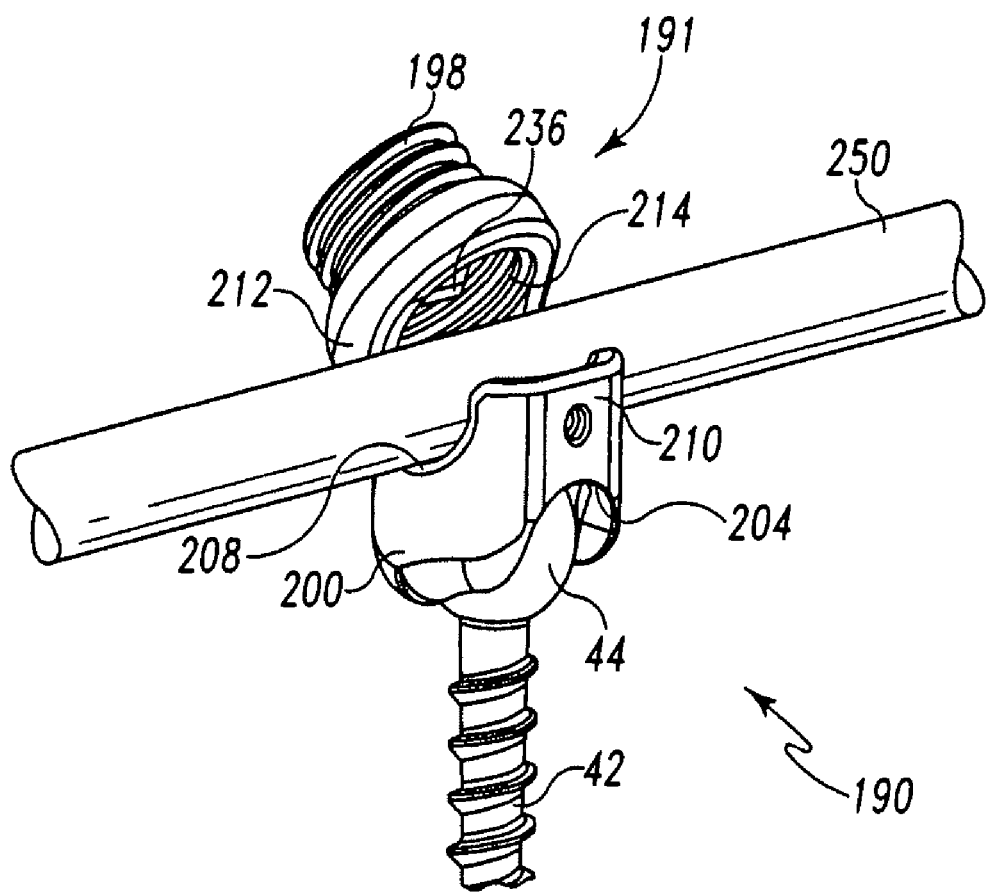
FIG. 19 is a perspective view of the pedicle screw construct of FIGS. 14-18 shown receiving a spinal rod.
Figure 20:
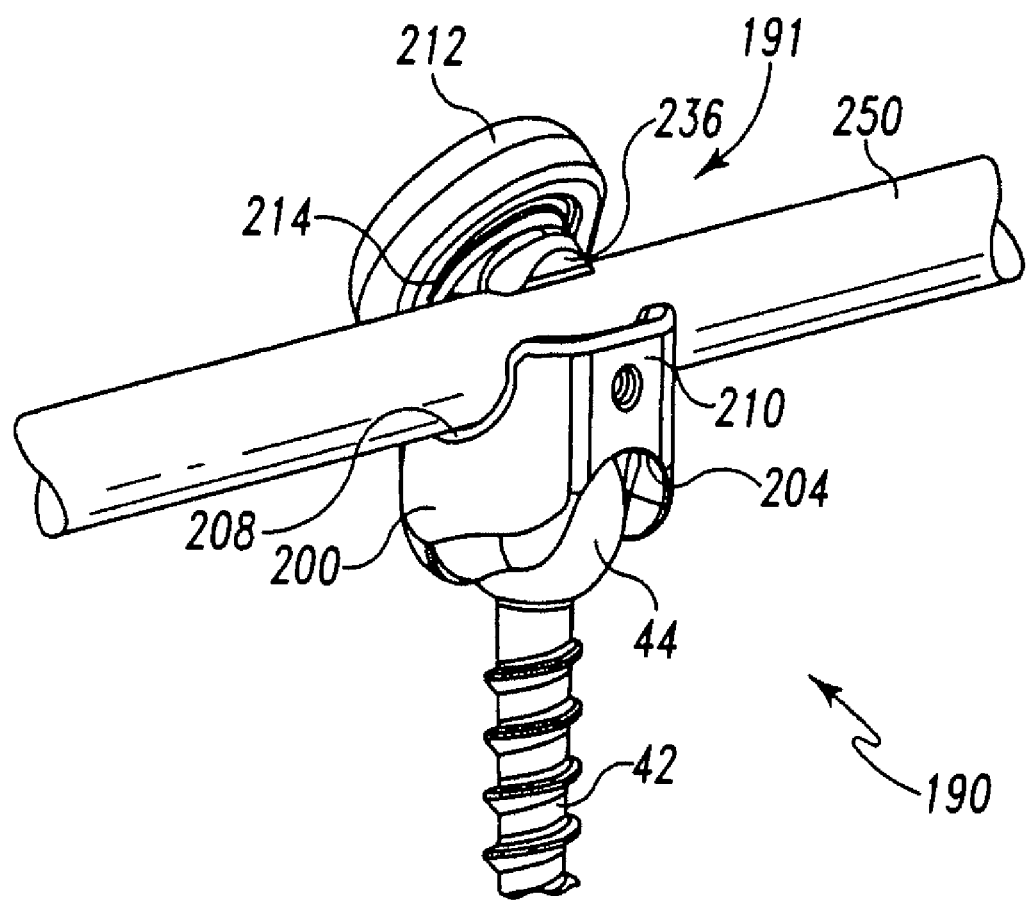
FIG. 20 is the perspective view of FIG. 19 illustrating the manner of loading the spinal rod.

FIG. 19 depicts the coupling construct 191 on the pedicle screw constituting the pedicle screw construct 190 having received a spinal rod 250. The coupling construct 191 is shown before fixation of the spinal rod to the coupling head 200 and before fixation of the orientation of the coupling head 200 relative to the screw head 44. FIG. 20 depicts the fixation of the spinal rod to the coupling head 200 and the fixation of the coupling head orientation relative to the screw head 44. The set screw 198 has been received in the bore of the top portion 212 such that the rod retention element has loaded or moved into pressure engagement with the rod 250. The nose 236 can be seen providing configured retention of the rod 250. It should be appreciated that while the screw is shown in a 0° position, not withstanding rotation of the head 200 relative to the screw, the screw may be positioned from 0° to approximately 90°.

Figure 21:
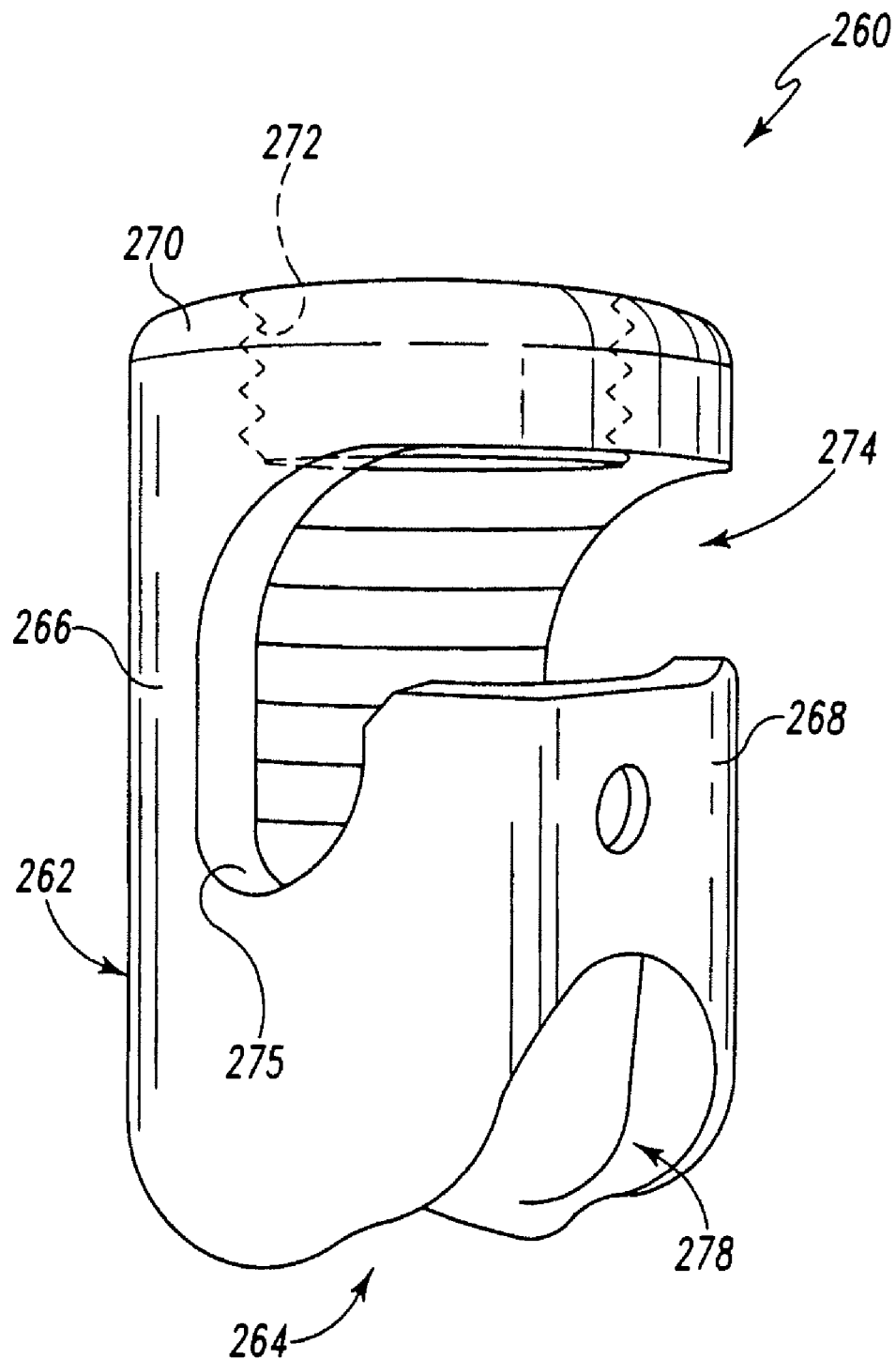
FIG. 21 is a perspective view of another embodiment of a pedicle screw construct head in accordance with the present principles.

Referring now to FIG. 21, there is depicted another embodiment of a coupling head generally designated 260. The coupling head 260 is similar to the coupling head 192 of the coupling construct 191, but rather provides a side or 90° entry into a rod channel 274. Particularly, the coupling head 260 is characterized by a body 262 having a generally tubular shape having a central bore 264 that extends from a configured end 278 (configured for 90°+screw angulation) to end 272. The bore 264 is threaded at end 272 to receive a set screw (e.g. set screw 198). An elongated neck 262 terminates in a rounded top portion 270. The top portion 270 is perpendicular to the bore 264 to provide side entry (approximately 90°) for the spinal rod relative to the axis of the bore (0°).

Figure 22:
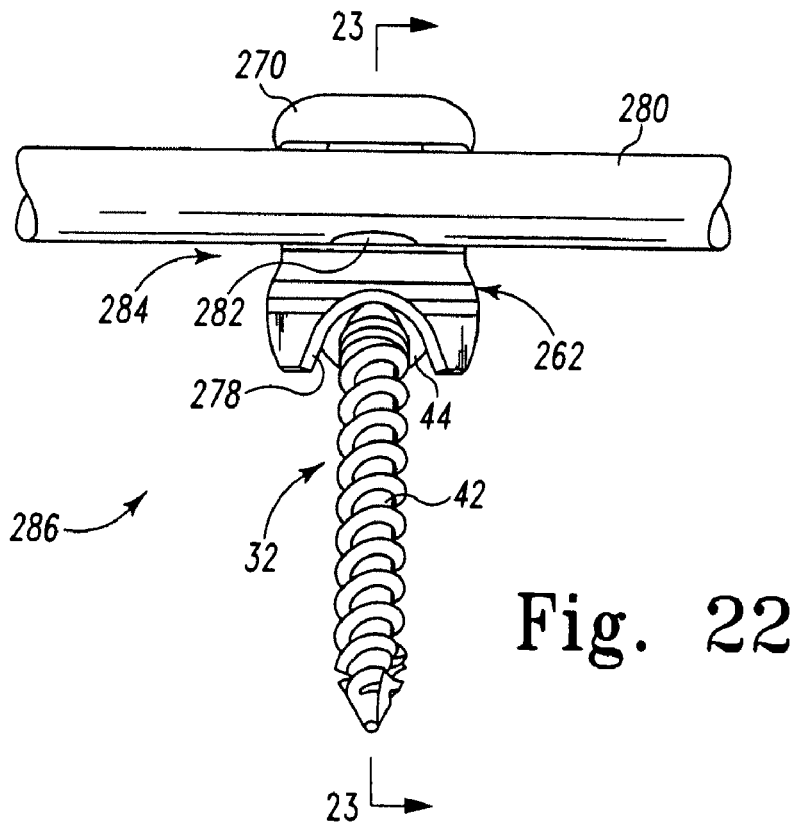
FIG. 22 is a front view of an assembled pedicle screw construct utilizing the head of FIG. 21 shown in receipt of a spinal rod before loading thereof.
Figure 23:
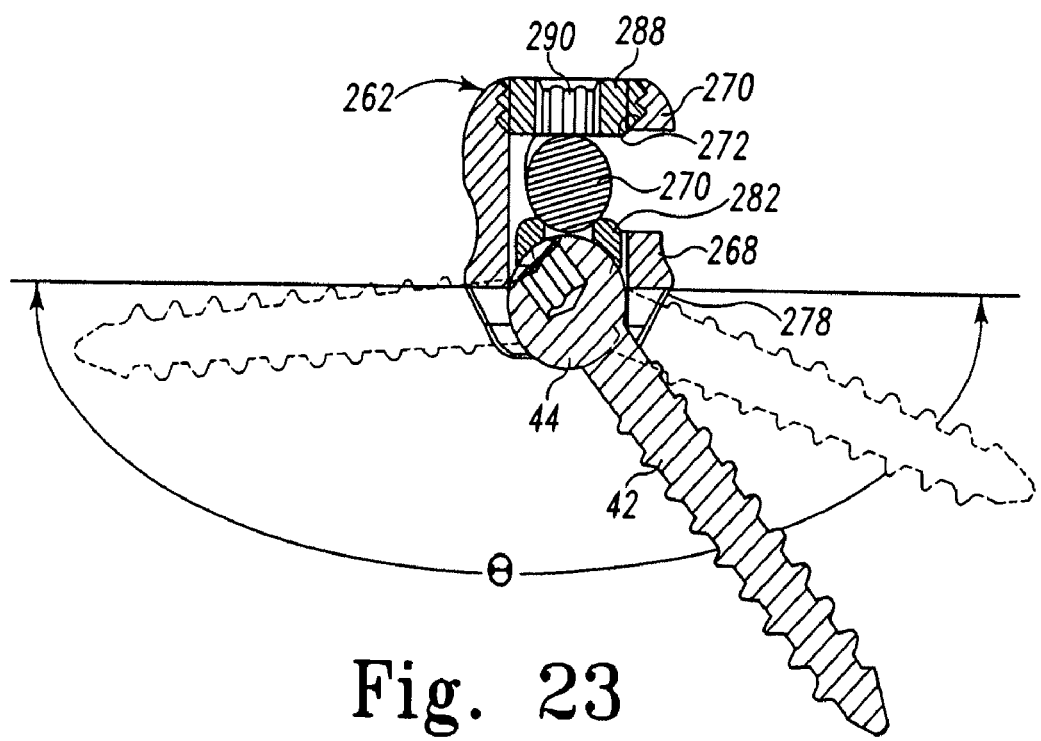
FIG. 23 is a sectional view of FIG. 22 taken along line 23-23 thereof, the pedicle screw of which is shown in various angular orientations relative to the head illustrating the range of angular orientations of the pedicle screw relative to the head in accordance with the principles of the present invention.

FIGS. 22 and 23 depict the coupling head 260 as a coupling construct and pedicle screw construct releasably fixedly holding or retaining a spinal rod 280. In addition to the set screw 288 having a configured driving socket 290, the coupling construct includes a collar 282 that fits over the pedicle screw head 44 and provides a seat for the rod 280. The collar 282 cradles the rod 280 to maintain the rod 280 in place. The set screw 288 provides pressure against the rod 280 which provides pressure against the collar 282 which provides pressure against the head 44 to releasably fix the rod 280 to the head 262 and the head 262 to the screw 32. Moreover, the configured opening 278 of the head 262 is sized to allow an approximately 180° range of motion of the head relative to the screw/screw shaft as represented for ease of understanding by the change in positions of the screw (90° on either side of the 0° position) as indicated by the angle θ in FIG. 23. The coupling head also rotates about the head 44.

It should be appreciated that the figures showing the pedicle screw in various orientations or positions illustrates the various orientations (or limits of a continuous range of orientations or positions) the coupling head or construct may assume in accordance with the present principles, since the pedicle screw will be fixed in orientation when implanted into a vertebra. As such, the coupling head or construct moves, pivots or folds with respect to the screw and/or screw shaft (axis). It can thus be understood that the coupling head/coupling head construct pivots or folds downwardly with respect to the pedicle screw shaft/axis. When implanted, the pedicle screw axis may be deemed a vertical, and therefore the head/construct preferably, but not necessarily, moves from a vertical (0°) or near vertical (−5°) position to a horizontal (45°) or near horizontal (±5°) position. It should also be appreciated that the elongated channel, slot or end of the coupling head/coupling head construct is preferably, but not necessarily, oriented substantially perpendicular to the longitudinal axis of a retained spinal rod. Thus the arc of movement of the coupling head or construct is along an arc that is perpendicular to the longitudinal axis of the spinal rod. In FIG. 23, for example, that range or arc of movement is given by θ.

The present invention provides advantages over the teachings of the prior art with respect to pedicle screw construct technology. The principles accompanying the present invention allows the present pedicle screw construct to be used with greater accuracy. This may ultimately increase the efficacy of an established procedure. The present pedicle screw constructs and/or coupling constructs used along with a bone screw, may utilize various types of spinal rods such as straight or pre-curved rods may be used. The rod may be bent or curved in one or more locations.

The subject constructs provide several key attributes not present in the prior art and not necessarily discussed above. The subject pedicle screw construct has the ability to reduce stack height by approximately 50% over prior pedicle screw constructs. Stack height is the overall total height of the installed construct. Such reduction in stack height reduces tissue distraction, reduces discomfort, and provides a reduction on construct loading that may lead to premature failure.

The subject pedicle screw construct also has the ability to fold (articulate) from a raised position of approximately −10° (±10°) to approximately 90°±10°. The pedicle screw construct is operative, configured and/or adapted to releasably lock into any articulation angle from the −10° (±10°) to approximately 90°±10° position. In one form, the subject pedicle screw construct also provides 360° rotation of the coupling member with respect to the bone screw thereof. The bone screw/coupling member also provides at least one other plane of relative motion.

The present coupling constructs, such as the coupling construct of FIGS. 15-23 allows the body or head thereof to be positioned relative to an implanted pedicle screw (and therefore the body or coupling construct relative to the pedicle screw) to receive a spinal rod in a top loading position while the body is at least in and/or within a −5° arc relative to a perpendicular of the pedicle screw (shaft). This allows the head to rotate about the pedicle screw in a folded state to at least and/or within a 45° arc relative to the pedicle screw.

During implantation, the head is angled straight up and down relative to the U-channel, the head is then angled parallel (through and to the at least 45° arc) to the horizon (at least perpendicular to the pedicle screw shaft) to receive the set screw. Thereafter, the head is folded over to where the back surface can be horizontal to the horizon in an effort to lock up the system. The system, however, can be locked in any arcuate and rotational orientation therebetween.

Use of the subject pedicle screw construct alleviates the need to use multiple systems to produce the same surgical outcome. The subject pedicle screw construct provides the surgeon with greater flexibility during the surgical procedure to adjust pathological anatomy. For example, current systems only allow several degrees of movement from the center to midline area. The subject pedicle screw construct allows the surgeon to place the bone screws thereof and then adjust the positioning of the coupling member (stabilization link) intra-operatively without removing the pedicle screws from the pedicle. The net effect is a more forgiving system.

The subject pedicle screw construct also provides the surgeon with the ability to adjust the system without disassembly. Particularly, adjustment of a connecting rod or of stack height can be accomplished without disassembling the pedicle construct and/or removing a pedicle screw thereof. Current "tulip" designed pedicle screw constructs require that during each adjustment the surgeon fully assembly the system. If several adjustments are necessary, the potential to strip out the threads within the tulip are high. If this happens, the entire pedicle screw would need to be removed, in which case the integrity of the whole construct is eroded. This is not the case with the subject pedicle screw construct.

The subject pedicle screw construct is intended for use with the spine. Particularly, the subject pedicle screw construct is intended (non-exclusively) for patients with the following indications:

When used as a pedicle screw system in skeletally mature patients;
  a. Severe (Grade 3 and 4) Spondylolisthesis at the L5-S1 joint;
  b. Patients receiving fusion using autogenous bone graft only;
  c. Patients who are having the device fixed or attached to the lumbar and sacral spine (L3 and below); and
  d. Patients who are having the device removed after the development of a solid fusion mass.

When used as a pedicle screw system in skeletally mature patients, it is intended to provide immobilization and stabilization of spinal segments, as an adjunct to fusion, in the (non-exclusive) treatment of the following acute and chronic instabilities or deformities of the cervical, thoracic, lumbar and sacral spine:
  a. Degenerative spondylolisthesis with object evidence of neurological impairment;
  b. Fracture;
  c. Dislocation;
  d. Scoliosis;
  e. Kyphosis;
  f. Spinal tumor; and
  g. Previously failed fusion (pseudoarthrosis).

Moreover, the subject spine fixation system, when used for anterolateral non-pedicle screw fixation to the spine, is (non-exclusively) intended for the following indications:
  a Degenerative disc disease (as defined as back pain of discogenic origin with degenerative disc confirmed by history and radiographic studies);
  b. Spinal stenosis;
  c. Spondylolisthesis;
  d. Spinal deformities (e.g. scoliosis, kyphosis and/or lordosis);
  e. Pseudoarthrosis;
  f. Tumor;
  g. Trauma (e.g. fracture or dislocation); and
  h. Previous failed fusion.

Still further, the subject spine fixation system/pedicle screw construct, when used for posterior non-pedicle screw fixation to the spine, is intended for the following indications:
  a. Degenerative disc disease (as defined as back pain of discogenic origin with degenerative disc confirmed by history and radiographic studies);
  b. Spinal stenosis;
  c. Spondylolisthesis;
  d. Spinal deformities (e.g. scoliosis, kyphosis and/or lordosis);
  e. Pseudoarthrosis;
  f. Tumor;
  g. Trauma (e.g. fracture or dislocation); and
  h. Previous failed fusion.

The subject spine fixation system or pedicle screw construct differs from the prior art in the following ways. Particularly, there is substantially greater surgeon flexibility when placing the bone screws. Due to the wider range of motion offered by the head or coupling member, the pedicle screws can be inserted and placed in the most favorable anatomical position. This can be done because the system is not constrained by the connecting rods or the range of motion offered by the heads.

The subject system, in one form, is locked into place using a taper lock mechanism which reduces the stress applied to the locking screw mechanism thereof. This is a critical advantage as competing devices are locked into place by utilizing a locking collar, rod and head interface. The present spine fixation system utilizes mechanical advantages of using dual tapered interfaces to apply virtually infinite locking force while minimizing thread shear stresses.

The subject system allows for intra-operative adjustment of the system without having to apply the locking mechanism or set screw. Due to the unique design of the head, a connecting rod can be inserted and retained without installing the locking mechanism. This saves time, allows for greater variability with placement and potentially will reduce the need to remove the screw and head due to stripped locking mechanism threads.

Range of motion of the subject invention is greater that the prior art. The present spine fixation system/pedicle screw construct articulate from center to midline $-10°+95°$. The range of motion cephalad and caudal (superior/inferior) is approximately $\pm 45°$. These ranges of motion surpass all currently available spine fixation systems by at least $10°$.

Reduction of stack height to reduce the stress, distraction and trauma on surrounding tissues. Also, reduced stack heights make the device inherently stronger, due to the reduced inertial moments placed on the device.

It should be appreciated that the above description is only exemplary of the principles of the subject invention. Therefore, other embodiments are contemplated and within the present scope.

The screw is loaded into the various connecting components from the top (i.e. top loading). However, while not shown, it is contemplated that the coupling or connection of the screw to the connecting component may be accomplished from the bottom (i.e. bottom loading). A bottom loading connecting component may allow for greater folding and/or flexibility of the connecting component relative to the screw.

While this invention has been described as having a preferred design, the present invention can be further modified within the spirit and scope of this disclosure. This application is therefore intended to cover any variations, uses, of adaptations of the invention using its general principles. Further, this application is intended to cover such departures from the present disclosure as come within known or customary practice in the art to which this invention pertains and that fall within the limits of the appended claims.

What is claimed is:

1. A pedicle screw coupling device for holding a spinal rod relative to a pedicle screw, the pedicle screw coupling device comprising:
    a coupling head having a bore therethrough and defining a first end sized to receive a pedicle screw shaft and a pedicle screw head of the pedicle screw and a second end sized to allow the pedicle screw shaft to pass through but rotatably retain the pedicle screw head, the coupling head further including a channel configured to receive the spinal rod;
    a collar releasably rotatably coupled directly to the coupling head;
    a sleeve received in the coupling head bore between the pedicle screw head and the collar, the sleeve having a first end abutting the pedicle screw head and a second end abutting the collar;
    a spinal rod retention element configured to be received through the collar and to fix the spinal rod received in the channel of the coupling head relative to the coupling head;
    wherein the collar applies pressure to the pedicle screw head through the sleeve to fix an orientation of the coupling head relative to the pedicle screw head responsive to the collar being rotatably coupled directly to the coupling head;
    wherein the fixation of the spinal rod relative to the coupling head is separate and independent of the fixation of the coupling head relative to the pedicle screw head.

2. The pedicle screw coupling device of claim 1 wherein the sleeve includes a sidewall having a taper extending from the second end to the first end.

3. The pedicle screw coupling device of claim 1 wherein the coupling head has undercut channels that mateably receive the collar in a snap fit fashion during fixation.

4. The pedicle screw coupling device of claim 1 wherein the coupling head has threads that mateably receive the collar during fixation.

5. The pedicle screw coupling device of claim 1 wherein the spinal rod channel of the coupling head maintains the spinal rod axially above the pedicle screw head.

6. The pedicle screw coupling device of claim 5 wherein the spinal rod is maintained spaced apart from the pedicle screw head.

7. The pedicle screw coupling device of claim 1 wherein the coupling head has a pair of grooves that mateably receive a pair of flanges on the collar during fixation.

8. The pedicle screw coupling device of claim 7 wherein the collar comprises a first detent that engages the sleeve when rotated.

9. The pedicle screw coupling device of claim 8 wherein the first detent is located on a bottom surface of the collar adjacent one of the pair of flanges, and wherein the collar comprises a second detent located on the bottom surface adjacent the other of the pair of flanges.

10. The pedicle screw coupling device of claim 9 wherein each of the detents comprises a ramped portion and a stop surface that are rotated into pressure engagement with an upper surface of the sleeve.

11. The pedicle screw coupling device of claim 9 wherein the spinal rod is received in the slot and retained against the first seating surface and the second seating surface.

12. The pedicle screw coupling device of claim 1 wherein the collar comprises a pair of notches sized to receive a tool for rotating the collar relative to coupling head.

13. The pedicle screw coupling device of claim 1 wherein the sleeve comprises a slot that defines a first seating surface and a second seating surface.

14. A coupling device for holding a spinal rod relative to a pedicle screw having a pedicle screw shaft and a pedicle screw head, the coupling device comprising:
    a coupling head having a bore and a channel, the bore having a first end sized to allow the pedicle screw shaft and the pedicle screw head to pass through and a second end sized to allow the pedicle screw shaft to pass through but rotatably retain the pedicle screw head, the channel configured to receive the spinal rod;
    a sleeve received in the bore of the coupling head and having a first end and a second end, the first end configured to abut the pedicle screw head;
    a collar releasably rotatably coupled directly to the coupling head and abutting the second end of the sleeve, wherein an angular orientation of the coupling head is fixed relative to the pedicle screw by pressure applied by the collar to the pedicle screw head through the sleeve responsive to the collar being rotatably coupled directly to the coupling head;
    a spinal rod retention element received through the collar to fix the spinal rod relative to the coupling head;
    wherein the angular orientation of the coupling head relative to the pedicle screw head is separately and releasably fixed independent of the releasable fixation of the spinal rod to the coupling head.

15. The coupling device of claim 14 wherein an exterior feature of the collar is coupled to an interior feature of the coupling head by a rotating movement of the collar relative to the coupling head.

16. The coupling device of claim 15 wherein the exterior feature of the collar comprises a flange and the interior feature of the coupling head comprises a groove.

17. The coupling device of claim 16 wherein the collar comprises a first detent that engages the sleeve when rotated.

18. The coupling device of claim 16 wherein the collar comprises a second detent, the first detent is located on a bottom surface of the collar adjacent one of the pair of flanges, and the second detent is located on the bottom surface adjacent the other of the pair of flanges.

19. The coupling device of claim 16 wherein each of the detents comprises a ramped portion and a stop surface that are rotated into pressure engagement with an upper surface of the sleeve.

* * * * *